US010918615B2

(12) United States Patent
Vaughn et al.

(10) Patent No.: US 10,918,615 B2
(45) Date of Patent: *Feb. 16, 2021

(54) FUMARATE ESTERS

(71) Applicant: Banner Life Sciences LLC, High Point, NC (US)

(72) Inventors: Jason M. Vaughn, Browns Summit, NC (US); Justin R. Hughey, Asheboro, NC (US); Tanesha Roberts, Greensboro, NC (US); Tatyana Dyakonov, Greensboro, NC (US); Sunil Agnihotri, Scarborough, ME (US); Aqeel A. Fatmi, High Point, NC (US)

(73) Assignee: BANNER LIFE SCIENCES LLC, High Point, NC (US)

( * ) Notice: Subject to any disclaimer, the term of this patent is extended or adjusted under 35 U.S.C. 154(b) by 166 days.

This patent is subject to a terminal disclaimer.

(21) Appl. No.: 16/129,860

(22) Filed: Sep. 13, 2018

(65) Prior Publication Data
US 2019/0015372 A1    Jan. 17, 2019

Related U.S. Application Data

(60) Continuation of application No. 15/686,352, filed on Aug. 25, 2017, now Pat. No. 10,098,863, which is a continuation-in-part of application No. 15/386,175, filed on Dec. 21, 2016, now Pat. No. 9,814,692, which is a continuation of application No. 15/248,506, filed on Aug. 26, 2016, now Pat. No. 9,636,318, which is a continuation-in-part of application No. 15/073,720, filed on Mar. 18, 2016, now Pat. No. 9,517,209, which is a division of application No. 14/840,072, filed on Aug. 31, 2015, now Pat. No. 9,326,947, which is a continuation-in-part of application No. 14/633,164, filed on Feb. 27, 2015, now Pat. No. 9,326,965.

(60) Provisional application No. 62/492,374, filed on May 1, 2017, provisional application No. 62/356,872, filed on Jun. 30, 2016, provisional application No. 62/300,941, filed on Feb. 29, 2016, provisional application No. 62/061,185, filed on Oct. 8, 2014, provisional application No. 62/011,604, filed on Jun. 13, 2014, provisional application No. 61/950,648, filed on Mar. 10, 2014, provisional application No. 61/946,233, filed on Feb. 28, 2014.

(51) Int. Cl.
| | | |
|---|---|---|
| A61K 31/225 | (2006.01) |
| A61P 25/00 | (2006.01) |
| A61K 9/10 | (2006.01) |
| A61K 9/00 | (2006.01) |
| A61K 47/46 | (2006.01) |
| A61K 47/12 | (2006.01) |
| A61K 47/44 | (2017.01) |
| A61K 47/32 | (2006.01) |
| A61K 47/14 | (2017.01) |
| A61K 9/48 | (2006.01) |
| A61K 45/06 | (2006.01) |
| A61P 25/28 | (2006.01) |

(52) U.S. Cl.
CPC .......... *A61K 31/225* (2013.01); *A61K 9/0053* (2013.01); *A61K 9/4808* (2013.01); *A61K 9/4858* (2013.01); *A61K 9/4866* (2013.01); *A61K 9/4875* (2013.01); *A61K 9/4891* (2013.01); *A61K 45/06* (2013.01); *A61P 25/28* (2018.01)

(58) Field of Classification Search
None
See application file for complete search history.

(56) References Cited

U.S. PATENT DOCUMENTS

| | | |
|---|---|---|
| 5,146,730 A | 9/1992 | Dietel |
| 5,424,332 A | 6/1995 | Speiser |
| 5,459,983 A | 10/1995 | Dietel |
| 6,355,676 B1 | 3/2002 | Joshi |
| 6,436,992 B1 | 8/2002 | Joshi |
| 6,482,516 B1 | 11/2002 | Dietel |
| 6,509,376 B1 | 1/2003 | Joshi |
| 7,157,423 B2 | 1/2007 | Joshi |

(Continued)

FOREIGN PATENT DOCUMENTS

| | | |
|---|---|---|
| EP | 0312697 A2 | 4/1989 |
| WO | 2000030622 | 6/2000 |

(Continued)

OTHER PUBLICATIONS

Gold et al., "Safety of a novel oral single-agent fumarate, BG00012, in patients with relapsing-remitting multiple sclerosis: results of a phase 2 study," Journal of Neurology 253(Suppl. 2): II144-II145 (2006).

Gullapalli, Journal of Pharmaceutical Science 99(10) 4107-4148 (2010).

Kappos et al., "BG00012, a novel oral fumarate, is effective in patients with relapsing-remitting multiple sclerosis", Multiple Sclerosis 2(Suppl. 1):S85 (2006).

Schilling et al., "Fumaric acid esters are effective in chronic experimental autoimmune encephalomyelitis and suppress macrophage infiltration," Clinical and Experimental Immunology 145(1):101-107 (2006).

(Continued)

*Primary Examiner* — Abigail Vanhorn
(74) *Attorney, Agent, or Firm* — Michael Best & Friedrich LLP

(57) ABSTRACT

Described herein are pharmaceutical compositions comprising one or more fumarate esters, processes for making the same, and compositions and methods for treating multiple sclerosis subjects with the compositions. In particular, oral pharmaceutical compositions comprising fumarate esters in liquid vehicles are described. One embodiment is an oral delayed release pharmaceutical dosage form comprising a soft capsule encapsulating an immediate releasing liquid comprising one or more fumarate esters.

12 Claims, 4 Drawing Sheets

(56) References Cited

U.S. PATENT DOCUMENTS

| | | | |
|---|---|---|---|
| 7,320,999 B2 | 1/2008 | Joshi | |
| 7,432,240 B2 | 10/2008 | Joshi | |
| 7,612,110 B2 | 11/2009 | Joshi | |
| 7,619,001 B2 | 11/2009 | Joshi | |
| 7,803,840 B2 | 9/2010 | Joshi | |
| 7,915,310 B2 | 3/2011 | Joshi | |
| 8,293,270 B2 | 10/2012 | Sukuru | |
| 8,333,989 B2 | 12/2012 | Sukuru | |
| 8,399,514 B2 | 3/2013 | O Neill | |
| 8,524,773 B2 | 9/2013 | Joshi | |
| 8,669,281 B1 | 3/2014 | Sanrame | |
| 8,669,282 B2 | 3/2014 | Zicker | |
| 8,685,445 B2 | 4/2014 | Hassan | |
| 8,759,393 B2 | 6/2014 | Joshi | |
| 9,090,558 B2 | 7/2015 | Sanrame | |
| 9,302,977 B2 | 4/2016 | Raillard | |
| 9,326,947 B1 | 5/2016 | Fatmi | |
| 9,326,965 B2 | 5/2016 | Fatmi | |
| 9,511,043 B2 | 12/2016 | Fatmi | |
| 9,517,209 B2 | 12/2016 | Fatmi | |
| 9,526,965 B2 | 12/2016 | Gatherer | |
| 9,566,259 B1 | 2/2017 | Hughey | |
| 9,636,318 B2 | 5/2017 | Hughey | |
| 9,636,319 B1 | 5/2017 | Hughey | |
| 9,814,691 B2 * | 11/2017 | Dyakonov | A61K 31/225 |
| 9,814,692 B2 * | 11/2017 | Vaughn | A61K 31/225 |
| 9,820,960 B2 * | 11/2017 | Dyakonov | A61K 9/4875 |
| 9,820,961 B2 * | 11/2017 | Vaughn | A61K 31/225 |
| 10,098,863 B2 * | 10/2018 | Vaughn | A61K 9/4808 |
| 10,105,335 B2 * | 10/2018 | Vaughn | A61K 31/225 |
| 10,105,336 B2 * | 10/2018 | Dyakonov | A61K 9/4875 |
| 10,105,337 B2 * | 10/2018 | Dyakonov | A61K 31/225 |
| 2003/0018072 A1 | 1/2003 | Joshi | |
| 2004/0054001 A1 | 3/2004 | Petzelbauer | |
| 2006/0051345 A1 | 3/2006 | Frohna | |
| 2006/0115527 A1 | 6/2006 | Hassan | |
| 2006/0165778 A1 | 7/2006 | Hassan | |
| 2007/0104778 A1 | 5/2007 | Ketsela | |
| 2007/0269507 A1 | 11/2007 | Sanchetto et al. | |
| 2008/0003282 A1 | 1/2008 | Soll | |
| 2008/0004344 A1 | 1/2008 | Nilsson | |
| 2008/0233185 A1 | 9/2008 | Joshi | |
| 2008/0299196 A1 | 12/2008 | Muller | |
| 2008/0300217 A1 | 12/2008 | Nilsson | |
| 2009/0304790 A1 | 12/2009 | Nilsson | |
| 2010/0034274 A1 | 2/2010 | Li | |
| 2010/0130607 A1 | 5/2010 | Gold | |
| 2010/0259906 A1 | 10/2010 | Chang | |
| 2010/0278879 A1 | 11/2010 | Manku | |
| 2010/0324327 A1 | 12/2010 | Lee | |
| 2011/0112196 A1 | 5/2011 | Lukashev | |
| 2012/0034274 A1 | 2/2012 | Rupp | |
| 2012/0165404 A1 | 6/2012 | Lukashev | |
| 2012/0259012 A1 | 10/2012 | Lukashev | |
| 2013/0115281 A1 | 5/2013 | Draper et al. | |
| 2013/0216615 A1 | 8/2013 | Goldman | |
| 2013/0259906 A1 | 10/2013 | Rupp | |
| 2013/0295169 A1 | 11/2013 | Goldman | |
| 2013/0302410 A1 | 11/2013 | Gold | |
| 2013/0303613 A1 | 11/2013 | Lukashev | |
| 2013/0315993 A1 | 11/2013 | Nilsson | |
| 2013/0316003 A1 | 11/2013 | Nilsson | |
| 2013/0317103 A1 | 11/2013 | Lukashev | |
| 2013/0324539 A1 | 12/2013 | Annamalai | |
| 2014/0037720 A1 | 2/2014 | Nilsson | |
| 2014/0037740 A1 | 2/2014 | Nilsson | |
| 2014/0056973 A1 | 2/2014 | Virsik | |
| 2014/0056978 A1 | 2/2014 | Karaborni | |
| 2014/0057917 A1 | 2/2014 | Virsik | |
| 2014/0057918 A1 | 2/2014 | Shreeniwas | |
| 2014/0065211 A1 | 3/2014 | Karaborni | |
| 2014/0066505 A1 | 3/2014 | Joshi | |
| 2014/0099364 A2 | 4/2014 | Nilsson | |
| 2014/0163100 A1 | 6/2014 | Dawson | |
| 2014/0179779 A1 | 6/2014 | Chao | |
| 2014/0193495 A1 | 7/2014 | Nilsson | |
| 2014/0199386 A1 | 7/2014 | Nilsson | |
| 2014/0199387 A1 | 7/2014 | Nilsson | |
| 2014/0199388 A1 | 7/2014 | Nilsson | |
| 2014/0199390 A1 | 7/2014 | Nilsson | |
| 2014/0199392 A1 | 7/2014 | Nilsson | |
| 2014/0199393 A1 | 7/2014 | Nilsson | |
| 2014/0200272 A1 | 7/2014 | Nilsson | |
| 2014/0200273 A1 | 7/2014 | Nilsson | |
| 2014/0200363 A1 | 7/2014 | Irdam | |
| 2014/0205659 A1 | 7/2014 | Nilsson | |
| 2014/0275048 A1 | 9/2014 | Sanrame | |
| 2014/0275205 A1 | 9/2014 | Sanrame | |
| 2014/0275250 A1 | 9/2014 | Cundy | |
| 2014/0323570 A1 | 10/2014 | Gold | |
| 2014/0348914 A9 | 11/2014 | Karaborni | |
| 2014/0348915 A9 | 11/2014 | Karaborni | |
| 2014/0350018 A9 | 11/2014 | Virsik | |
| 2014/0378542 A1 | 12/2014 | Karaborni | |
| 2015/0024049 A1 | 1/2015 | Nilsson | |
| 2015/0079180 A1 | 3/2015 | Karaborni | |
| 2015/0132747 A1 | 5/2015 | Lukashev | |
| 2015/0190360 A1 | 7/2015 | Cundy | |
| 2015/0209318 A1 | 7/2015 | Goldman | |
| 2015/0246016 A1 | 9/2015 | Fatmi | |
| 2015/0252013 A1 | 9/2015 | Annamalai | |
| 2015/0307914 A9 | 10/2015 | Virsik | |
| 2015/0366803 A1 | 12/2015 | O Neill | |
| 2016/0101059 A1 | 4/2016 | Fatmi | |
| 2016/0199335 A1 | 7/2016 | Fatmi | |
| 2016/0199336 A1 | 7/2016 | Fatmi | |
| 2017/0056359 A1 | 3/2017 | Hughey | |
| 2017/0056360 A1 | 3/2017 | Hughey | |
| 2017/0071891 A1 | 3/2017 | Fatmi | |
| 2017/0100360 A1 | 4/2017 | Fatmi | |
| 2017/0100361 A1 | 4/2017 | Hughey | |
| 2017/0100362 A1 | 4/2017 | Hughey | |
| 2017/0231942 A1 | 8/2017 | Vaughn et al. | |
| 2019/0008818 A1 * | 1/2019 | Dyakonov | A61K 47/14 |
| 2019/0015373 A1 * | 1/2019 | Vaughn | A61K 31/225 |
| 2019/0015374 A1 * | 1/2019 | Dyakonov | A61K 9/4866 |

FOREIGN PATENT DOCUMENTS

| | | |
|---|---|---|
| WO | 2000030622 A2 | 6/2000 |
| WO | 2002055063 A2 | 7/2002 |
| WO | 2002055066 A1 | 7/2002 |
| WO | 2002055067 A2 | 7/2002 |
| WO | 2004030658 A1 | 4/2004 |
| WO | 2005009409 A2 | 2/2005 |
| WO | 2005023241 A1 | 3/2005 |
| WO | 2006023629 A2 | 3/2006 |
| WO | 2006023649 A2 | 3/2006 |
| WO | 2006023651 A2 | 3/2006 |
| WO | 2006036371 A2 | 4/2006 |
| WO | 2006037342 A2 | 4/2006 |
| WO | 2007042034 A1 | 4/2007 |
| WO | 2007042035 A2 | 4/2007 |
| WO | 2008096271 A2 | 8/2008 |
| WO | 2010022177 A2 | 2/2010 |
| WO | 2010079222 A1 | 7/2010 |
| WO | 2010126605 A1 | 11/2010 |
| WO | 2012013331 A2 | 2/2012 |
| WO | 2012162669 A1 | 11/2012 |
| WO | 2012170923 A1 | 12/2012 |
| WO | 2013076216 A1 | 5/2013 |
| WO | 2013090799 A1 | 6/2013 |
| WO | 2013092269 A1 | 6/2013 |
| WO | 2013112859 A1 | 8/2013 |
| WO | 2013119677 A1 | 8/2013 |
| WO | 2013148690 A1 | 10/2013 |
| WO | 2013158969 A1 | 10/2013 |
| WO | 2014028299 A1 | 2/2014 |
| WO | 2014031844 A1 | 2/2014 |
| WO | 2014031892 A1 | 2/2014 |
| WO | 2014031894 A1 | 2/2014 |
| WO | 2014031897 A1 | 2/2014 |
| WO | 2014031901 A1 | 2/2014 |
| WO | 2014143146 A1 | 9/2014 |

(56) References Cited

FOREIGN PATENT DOCUMENTS

| WO | 2014190056 A2 | 11/2014 |
|---|---|---|
| WO | 2014197860 A1 | 12/2014 |
| WO | 2015017762 A1 | 2/2015 |
| WO | 2015028472 A1 | 3/2015 |
| WO | 2015028473 A1 | 3/2015 |
| WO | 2015042294 A1 | 3/2015 |
| WO | 2015044853 A2 | 4/2015 |
| WO | 2015086467 A1 | 6/2015 |
| WO | 2015089420 A1 | 6/2015 |
| WO | 2015105757 A1 | 7/2015 |
| WO | 2015128492 A1 | 9/2015 |
| WO | 2015130998 A1 | 9/2015 |
| WO | 2016057133 A1 | 4/2016 |
| WO | 2017040272 A1 | 3/2017 |

OTHER PUBLICATIONS

Schimrigk et al., "Oral fumaric acid esters for the treatment of active multiple sclerosis: an open-label, baseline-controlled pilot study," European J. Neurology 13(6): 604-610 (2006).
Sheikh et al., "Tolerability and pharmacokinetics of delayed-release dimethyl fumarate administered with and without aspirin in healthy volunteers," Clinical Therapeutics 35(10): 1582-1594 (2013).
TECFIDERA® Prescribing Information Mar. 2013 (BIOGEN IDEC).
Verma, R.K., et al., "Formulation Aspects in the Development of Osmotically Controlled Oral Drug Delivery Systems," Journal of Controlled Release, 79: 7-27 (2002).
Yeh et al., "Effect of Medium-Chain Glycerides on Physiological Properties of Rabbit Intestinal Epitheliun1 in Vitro," Pharma. Res. 11(8): 1148-1154 (1994).
Canadian Patent Office Action for Application No. 2,962,916 dated Jul. 16, 2020 (4 pages).

* cited by examiner

FUMARATE ESTERS

CROSS REFERENCE TO RELATED APPLICATIONS

This application is a continuation of U.S. patent application Ser. No. 15/686,352, filed on Aug. 25, 2017, which claims benefit of priority under 35 U.S.C. § 119 to U.S. Provisional Patent Application No. 62/492,374, filed on May 1, 2017 and is a continuation-in-part of U.S. patent application Ser. No. 15/386,175, filed Dec. 21, 2016, which is a continuation of U.S. patent application Ser. No. 15/248,506, filed on Aug. 26, 2016, now U.S. Pat. No. 9,636,318 and which claims benefit of priority under 35 U.S.C. § 119 to U.S. Provisional Patent Application Nos. 62/356,872, filed on Jun. 30, 2016 and 62/300,941, filed on Feb. 29, 2016, which is a continuation-in-part of U.S. patent application Ser. No. 15/073,720, filed on Mar. 18, 2016, now U.S. Pat. No. 9,517,209, which is a division of U.S. patent application Ser. No. 14/840,072, filed on Aug. 31, 2015, now U.S. Pat. No. 9,326,947, which is a continuation-in-part of U.S. patent application Ser. No. 14/633,164, filed on Feb. 27, 2015, now U.S. Pat. No. 9,326,965 and which claims benefit of priority under 35 U.S.C. § 119 to U.S. Provisional Patent Application Nos. 61/946,233, filed on Feb. 28, 2014; 61/950,648, filed on Mar. 10, 2014; 62/011,604, filed on Jun. 13, 2014; and 62/061,185, filed on Oct. 8, 2014. Each of the foregoing applications are individually incorporated herein in their entirety by express reference thereto.

TECHNICAL FIELD

Described herein are pharmaceutical compositions comprising one or more fumarate esters, processes for making the same, and compositions and methods for treating multiple sclerosis subjects with the compositions. In particular, oral pharmaceutical compositions comprising fumarate esters in liquid vehicles are described. One embodiment is an oral delayed release pharmaceutical dosage form comprising a soft capsule encapsulating an immediate releasing liquid comprising one or more fumarate esters.

BACKGROUND

Fumarate esters, including dialkyl fumarates and monoalkyl fumarates are pharmacologically active organic substances useful for treating hyperproliferative, inflammatory, or autoimmune disorders. Both dimethyl fumarate (DMF) and monomethyl fumarate (MMF) activate the nuclear factor erythroid-derived 2-like (Nrf2) pathway in vitro and in vivo in humans. The Nrf2 pathway is involved in the cellular response to oxidative stress. MMF has also been identified as a nicotinic acid receptor agonist in vitro.

TECFIDERA® (dimethyl fumarate) is indicated for the treatment of patients with relapsing-remitting forms of multiple sclerosis. See TECFIDERA® Prescribing Information, January 2017 at 2 (Biogen Inc.), which is incorporated herein in its entirety for the teachings thereof. TECFIDERA® is formulated as hard gelatin delayed-release capsules containing 120 mg or 240 mg of enterically coated DMF minitablets.

Upon oral ingestion, one methyl moiety of DMF is hydrolysed by esterases to form MMF, the bioactive metabolite. After absorption, MMF is believed to interact with immunocytes in the bloodstream. The primary plasma metabolites of DMF are MMF, fumaric acid, citric acid, and glucose. Monomethyl fumarate is further metabolized in the tricarboxylic acid cycle to carbon dioxide and water.

Fumarate esters produce various undesirable side effects, including flushing, headaches, dizziness, eructation, nausea, vomiting, abdominal or intestinal cramps, and diarrhea. High concentrations of the drug released in the stomach are believed to be responsible for such side effects.

Accordingly, it is desirable to develop oral formulations of fumarate esters that provide enhanced bioavailability and lower doses of fumarate esters as compared to TECFIDERA® and that are equally efficacious for treating multiple sclerosis, psoriasis, or other neurodegenerative, hyperproliferative, inflammatory, or autoimmune disorders.

SUMMARY

One embodiment described herein is an oral pharmaceutical composition comprising about 60 mg to about 200 mg of one or more fumarate esters in an immediate releasing single-phase non-aqueous liquid vehicle. In one aspect, the fumarate ester comprises dimethyl fumarate, monomethyl fumarate, a pro-drug of monomethyl fumarate, or a combination thereof. In another aspect, the fumarate ester comprises dimethyl fumarate. In another aspect, the fumarate ester comprises monomethyl fumarate. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the composition is encapsulated in soft capsule. In another aspect, the composition is encapsulated in an enterically coated soft capsule. In another aspect, the fumarate ester comprises about 80 mg to about 100 mg. In another aspect, the fumarate ester comprises about 160 mg to about 200 mg. In another aspect, upon administration to a subject, the composition activates a nuclear factor erythroid-derived 2-like (Nrf2) dependent pathway.

Another embodiment described herein is a pharmaceutical dosage form comprising a soft capsule and bout 85 mg to about 100 mg of one or more fumarate esters in an immediate releasing single-phase non-aqueous liquid vehicle. In one aspect, the fumarate ester comprises dimethyl fumarate, monomethyl fumarate, a pro-drug of monomethyl fumarate, or a combination thereof. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the soft capsule is enterically coated. In another aspect, administration of two dosage forms to a subject provides pharmacokinetic parameters that are bioequivalent to a single 240 mg dose of dimethyl fumarate. In another aspect, the 240 mg dose of dimethyl fumarate comprises a delayed release capsule comprising a plurality of enterically coated minitablets. In another aspect, the dosage form releases about 50% of the fumarate ester after about 50 min to about 65 min in sodium phosphate, pH 6.8, in a USP Apparatus 2 at 37° C. In another aspect, contemporaneous administration of two dosage forms to a subject provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr ng/mL; (e) a mean plasma monomethyl fumarate $AUC_{\%\ ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a pharmaceutical dosage form comprising a soft capsule and bout 160 mg to about 200 mg of one or more fumarate esters in an immediate releasing single-phase non-aqueous liquid vehicle. In one aspect, the fumarate ester comprises dimethyl fumarate, monomethyl fumarate, a pro-drug of monomethyl fumarate, or a combination thereof. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the soft capsule is enterically coated. In another aspect, administration of one dosage form to a subject provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr·ng/mL; (e) a mean plasma monomethyl fumarate $AUC_{\%\ ex}$ of about 0.86%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a method for treating or reducing symptoms of multiple sclerosis in a subject comprising administering to a subject in need thereof a pharmaceutical composition comprising about 60 mg to about 200 mg of one or more fumarate esters in an immediate releasing single-phase non-aqueous liquid vehicle. In one aspect, the fumarate ester comprises dimethyl fumarate, monomethyl fumarate, a pro-drug of monomethyl fumarate, or a combination thereof. In another aspect, the fumarate ester comprises dimethyl fumarate. In another aspect, the fumarate ester comprises monomethyl fumarate. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the composition is encapsulated in soft capsule. In another aspect, the composition is encapsulated in an enterically coated soft capsule. In another aspect, the fumarate ester comprises about 80 mg to about 100 mg. In another aspect, the fumarate ester comprises about 160 mg to about 200 mg. In another aspect, upon administration, the composition activates a nuclear factor erythroid-derived 2-like (Nrf2) dependent pathway.

Another embodiment described herein is a method for treating or reducing symptoms of multiple sclerosis in a subject comprising administering to a subject in need thereof one or more pharmaceutical dosage forms comprising about 80 mg to about 100 mg of one or more fumarate esters in an immediate releasing single-phase non-aqueous liquid vehicle. In one aspect, the fumarate ester comprises dimethyl fumarate. In another aspect, the fumarate ester comprises monomethyl fumarate. In another aspect, contemporaneous administration to a subject of two dosage forms provides pharmacokinetic parameters that are bioequivalent to a single 240 mg dose of dimethyl fumarate. In another aspect, the 240 mg dose of dimethyl fumarate comprises a delayed release capsule comprising a plurality of enterically coated minitablets. In another aspect, contemporaneous administration to a subject of two dosage forms provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr ng/mL; (d) a mean plasma monomethyl fumarate $AUC_{0 \to \infty}$ of about 3080 hr·ng/mL; (e) a mean plasma monomethyl fumarate $AUC_{\%\ ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a method for treating or reducing symptoms of multiple sclerosis in a subject comprising administering to a subject in need thereof a pharmaceutical dosage from comprising about 160 mg to about 200 mg of one or more fumarate esters in an immediate releasing single-phase non-aqueous liquid vehicle. In one aspect, the fumarate ester comprises dimethyl fumarate. In another aspect, the fumarate ester comprises monomethyl fumarate. In another aspect, administration of one dosage form to a subject provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr ng/mL; (e) a mean plasma monomethyl fumarate $AUC_{\%\ ex}$ of about 0.86%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a method for treating or reducing symptoms of multiple sclerosis in a subject comprising administering to a subject in need thereof about 340 mg to about 400 mg per day of monomethyl fumarate or dimethyl fumarate in an immediate releasing single-phase non-aqueous liquid vehicle. In one aspect, administration comprises a single dose of about 170 mg to about 200 mg of dimethyl fumarate or monomethyl fumarate twice per day. In another aspect, administration comprises contemporaneously administering two doses of about 85 mg to about 100 mg of dimethyl fumarate or monomethyl fumarate twice per day.

Another embodiment described herein is a method for treating or reducing symptoms of multiple sclerosis in a subject comprising administering to a subject in need thereof about 170 mg to about 200 mg of dimethyl fumarate or monomethyl fumarate in an immediate releasing single-phase non-aqueous liquid vehicle that provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\%\ ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is an oral pharmaceutical composition comprising about 85 mg to about 100 mg of dimethyl fumarate or monomethyl fumarate in an immediate releasing single-phase non-aqueous liquid vehicle.

DETAILED DESCRIPTION

Figure 1:
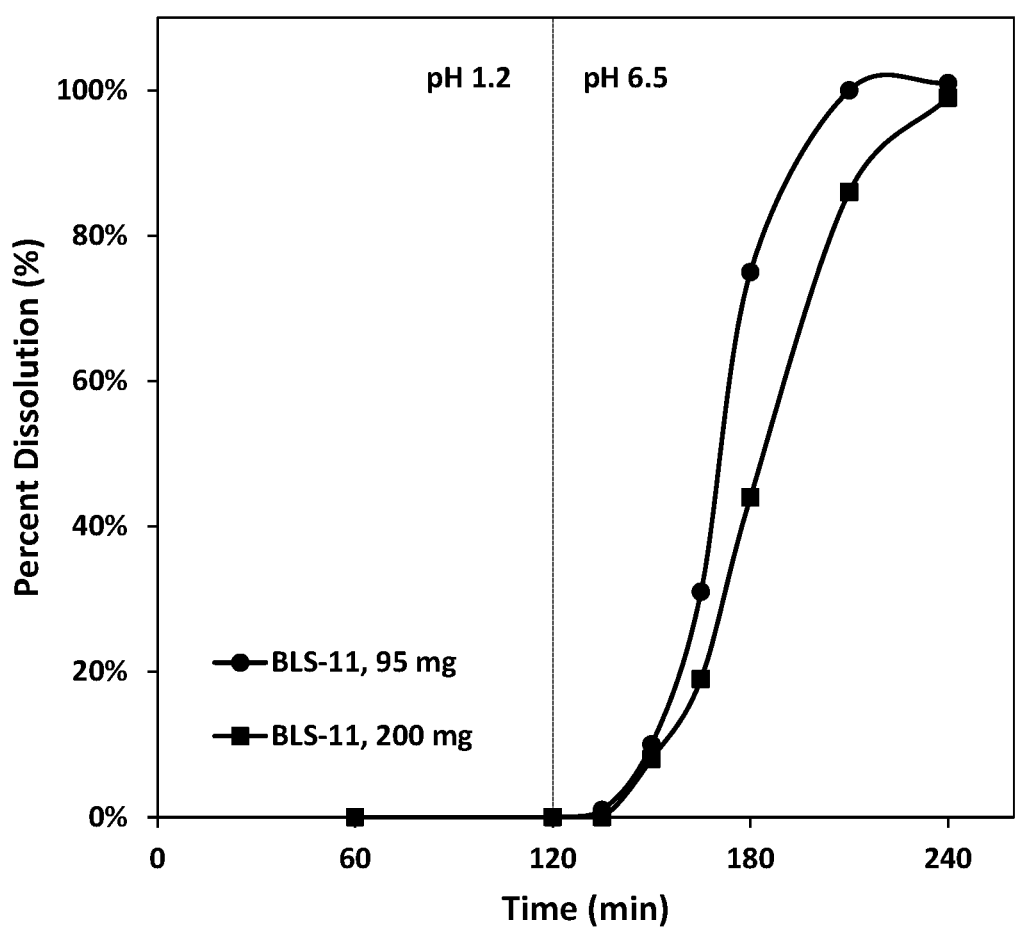
FIG. 1 shows two-stage dissolution experiments of dosage forms shown in Table 9.

Described herein are pharmaceutical compositions of mono- and di-alkyl fumarate esters, such as dimethyl fumarate, monomethyl fumarate, pro-drugs of monomethyl fumarate, other pharmacologically active fumarate esters, or combinations thereof.

The pharmaceutical compositions described herein provide one or more fumarate esters or pro-drugs thereof in liquid vehicles. In one embodiment, the composition comprises a single-phase liquid. In another embodiment, the composition comprises a hydrophobic liquid, a hydrophilic liquid, or a combination thereof. In another embodiment, the composition comprises a lipophilic liquid or a lipid liquid. In another embodiment, the composition comprises an aqueous liquid or a hydrophilic, non-aqueous liquid. In another embodiment, the composition comprises a solution of fumarate ester(s), a suspension of fumarate ester(s), or a combination thereof. In one aspect, the composition comprises an emulsion of hydrophilic and hydrophobic vehicles. In one aspect, the composition comprises a fluid, a viscous fluid, a colloid, gel, semisolid, or solid.

In one embodiment described herein, the fumarate ester pharmaceutical composition is a liquid encapsulated within a soft capsule shell. In another embodiment described herein, the fumarate ester pharmaceutical composition is a liquid encapsulated within a hard capsule shell. In another embodiment, the capsule is a soft capsule coated with an enteric coating and one or more subcoatings or top coatings. In another embodiment described herein, the composition is encapsulated in a hard capsule or an enteric hard capsule. In another embodiment described herein, the composition is encapsulated in a hard capsule comprising an enteric coating and one or more subcoatings or top coatings. In another embodiment described herein, the fumarate ester is in the form of a solution or suspension of solid microparticles of defined size in a lipid or lipophilic vehicle. In some aspects described herein, the lipid or lipophilic vehicle may comprise one or more hydrophilic polymers or species, but as described herein, the vehicle is considered a lipid or lipophilic vehicle.

As used herein, the term "fumarate ester" refers to any pharmacologically active mono- or di-alkyl fumarate ester, such as monomethyl fumarate, dimethyl fumarate, or other fumarate esters, acids, salts, pro-drugs of monomethyl fumarate, derivatives thereof, combinations, or mixtures of any of the foregoing. Fumarate ester as used herein also comprises prodrugs that are metabolized to monomethyl fumarate after administration to a subject.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The term "dose" as used herein denotes any form of the active ingredient formulation that contains an amount sufficient to produce a therapeutic effect with a single administration.

The term "dosage" as used herein refers to the administering of a specific amount, number, and frequency of doses over a specified period of time, typically 1 day.

The term "dosage form" as used herein refers to any pharmaceutical composition described herein in a form that can be administered to a subject. The dosage form used herein is for oral administration. Exemplary dosage forms described herein include capsules, hard capsules, soft capsules, enteric soft capsules, coated soft capsules, suspensions, solutions emulsions, or the like.

The term "soft capsule" or "soft gel capsule" as used herein refers to a capsule comprising one or more film-forming polymers that is capable of encapsulating a "matrix" or "fill" comprising pharmaceutically acceptable excipients and one or more active pharmaceutical ingredients.

The term "enteric soft capsule" as used herein refers to a soft capsule comprising one or more enteric polymers in the shell or a soft capsule that has been coated with one or more enteric coatings that are applied to the external surface of the capsule as described herein. The coated soft capsule may have one or more subcoatings applied prior to the application of the enteric coating.

The terms "matrix," "fill," or "matrix fill" as used herein refer to a composition comprising one or more active pharmaceutical ingredients that is encapsulated within a capsule. Often the matrix comprises a vehicle, one or more active pharmaceutical ingredients, and one or more pharmaceutically acceptable excipients. In one aspect described herein, the matrix is a liquid and comprises a lipid or lipophilic liquid comprising one or more fumarate esters.

The terms "active pharmaceutical ingredient load" or "drug load" as used herein refers to the quantity (mass) of the active pharmaceutical ingredient comprised in a single soft capsule fill.

The terms "formulation" or "composition" as used herein refers to the drug in combination with pharmaceutically acceptable excipients. This term includes orally administrable formulations as well as formulations administrable by other means.

The term "titration" as used herein refers to the incremental increase in drug dosage to a level that provides the optimal therapeutic effect.

The term "immediate release" as used herein refers to a composition that releases an active ingredient after a short period of time, typically within about 10 to 30 min.

The term "delayed release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under specific physiological conditions, or in a specific condition in an vitro test. In one aspect as used herein, delayed release refers to the ability of a dosage form to remain intact in the stomach or in vitro at a pH of about 1.2, and then begin releasing the active ingredient in the duodenum or in vitro at a pH of about 6.8 after a short period of time.

The term mean "particle size distribution" (PSD) as used herein refers to the mean particle size from a statistical distribution of a range of particle sizes as described herein. The distribution may be a Gaussian, normal distribution, or a non-normal distribution. The terms such as "d90," "d50," and "d10" refer to the percentage (e.g., 90%, 50%, or 10%, respectively) of particle sizes that are less than a specified size, range, or distribution. For example, "d90≤100 μm" means that 90% of the particle within a distribution are less than or equal to 100 μm.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for greater than one dose of the pharmaceutical compositions described herein. In one aspect, the "$AUC_{overall}$" refers to the combined area under the blood concentration versus time curve for at least two doses of the pharmaceutical compositions described herein.

The terms "bioequivalence" or "bioequivalent" as used herein refer to a drug product or dosage form that has highly similar release and systemic absorption as compared to a reference drug. The U.S. Food, Drug and Cosmetic Act (21 U.S.C. § 505(j)(8)(B)(i)) provides that a drug is bioequivalent to a reference listed drug (RLD) if: "the rate and extent of absorption of the drug do not show a significant difference from the rate and extent of absorption of the listed drug when administered at the same molar dose of the therapeutic ingredient under similar experimental conditions in either a single dose or multiple doses."

The phrase "enhanced bioavailability" as used herein refers to the increased proportion of an active pharmaceutical ingredient that enters the systemic circulation when introduced into the body as compared to a reference active pharmaceutical's bioavailability. Bioavailability can be determined by comparing the rate and extent of absorption of a drug with a reference drug when administered at the same molar dose of the active therapeutic ingredient under similar experimental conditions in either a single dose or multiple doses. Typical pharmacokinetic parameters can be used to demonstrate enhanced bioavailability compared to the reference drug.

The term "treating" refers to administering a therapy in an amount, manner, or mode effective (e.g., a therapeutic effect) to improve a condition, symptom, disorder, or parameter associated with a disorder, or a likelihood thereof.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to mass (or weight, w/w) percent unless noted otherwise.

The term "about" as used herein refers to any values, including both integers and fractional components that are within a variation of up to +10% of the value modified by the term "about."

As used herein, "a" or "an" means one or more unless otherwise specified.

Terms such as "include," "including," "contain," "containing," "having," and the like mean "comprising."

The term "or" can be conjunctive or disjunctive.

One embodiment described herein is a pharmaceutical composition comprising one or more fumarate esters for treating multiple sclerosis or other neurological disorders. Particles or micronized powders of one or more fumarate esters can be suspended or solvated in various solutions. The solutions can comprise lipids or lipophilic liquids or aqueous or hydrophilic liquids, or combinations thereof. Such liquids can be encapsulated in capsules, such as hard or soft capsules. In one embodiment, the pharmaceutical composition comprises a non-aqueous, single-phase, flowable liquid. In one embodiment, the pharmaceutical composition comprises a liquid comprising one or more lipid liquids, lipophilic liquids, hydrophilic liquids, or a combination thereof. In one embodiment, the pharmaceutical composition comprises a liquid comprising one or more lipid liquids, lipophilic liquids, or a combination thereof. In one embodiment, the pharmaceutical composition comprises a liquid comprising one or more lipophilic liquids, hydrophilic liquids, or a combination thereof. In one embodiment, the pharmaceutical composition comprises a liquid comprising one or more lipid liquids.

Another embodiment described herein, is an immediate release pharmaceutical composition comprising one or more fumarate esters for treating multiple sclerosis or other neurological disorders. Another embodiment is a delayed release pharmaceutical composition comprising a soft capsule shell encapsulating an immediate release liquid fill comprising one or more fumarate esters. Another embodiment is a delayed release pharmaceutical composition comprising capsule shell coated with one or more subcoatings, one or more enteric coatings, and one or more topcoating moisture barriers encapsulating an immediate release liquid fill comprising one or more fumarate esters. In one aspect, the pharmaceutical composition comprises one or more fumarate esters in an immediate releasing liquid that is encapsulated in an enteric soft capsule that provides delayed release of the fumarate ester in the intestines. In one aspect, the enteric soft capsule is a soft capsule that is coated with one or more enteric polymers. In another aspect, the soft capsule is additionally coated with a moisture barrier that improves the integrity of the capsule and eliminates cosmetic defects such as dimpling, flattening, or capsules sticking to each other.

The fumarate ester particles described herein (e.g., dimethyl fumarate or monomethyl fumarate, or prodrugs of monomethyl fumarate) may be generated by any particle size reduction or particle growth methodology known to one having ordinary skill the art. Exemplary and non-limiting methods comprise "top-down" reductions in particle size including mechanical micronization techniques, where larger particles are comminuted into smaller particles by jet milling, ball milling, or high-pressure homogenization; or particle engineering techniques such as cryogenic spraying or crystal engineering. In addition, "bottom-up" processing may be used to prepare suitable particle sizes as described herein using dual solvent/anti-solvent rapid precipitation techniques. See, *Handbook of Pharmaceutical Granulation Technology*, CRC Press, 3rd Edition, 2010, which is incorporated by reference herein for teachings related to generating pharmaceutical particles. In one aspect described herein, fumarate ester particles of a specified size distribution are produced using milling.

In another embodiment, the pharmaceutical composition comprises liquid fills for fumarate esters, such as dimethyl fumarate, monomethyl fumarate, prodrugs thereof, or derivatives thereof, based on lipids or lipophilic vehicles or hydrophilic vehicles. Some of the described matrices have a hydrophobic (lipophilic) surface in contact with the hydrophilic soft capsule shell to minimize any potential shell-fill interactions, such as when soft capsules are filled with hydrophilic vehicles. In other aspects, the fumarate esters are suspended in non-aqueous hydrophilic solutions containing one or more hydrophilic polymers such as polyvinyl pyrrolidone, polyethylene glycols, propylene glycols, polyoxyl 40 hydrogenated castor oil (e.g., glyceryl polyethylene glycol oxystearate, PEG-40 hydrogenated castor oil; Cremophor® RH 40), or combinations thereof.

Described herein are methods for manufacturing liquid fills comprising fumarate esters, such as dimethyl fumarate, monomethyl fumarate, prodrugs thereof, or derivatives thereof, in a controlled release soft capsule in the form of a suspension, where part or all of the fumarate ester is suspended within the composition. Also provided are compositions and formulations where the fumarate ester is incorporated into a single-phase liquid vehicle.

Also described herein are methods for manufacturing liquid fills comprising fumarate esters or derivatives thereof, in a delayed release soft capsule in the form of a solution and or suspension, where part or all of the fumarate ester is dissolved and/or suspended within the composition.

Another embodiment described herein is a delayed release capsule having a shell and a fill, wherein the fill includes a lipid or lipophilic liquid vehicle comprising a suspension or solution of solid particles of one or more fumarate esters such as dimethyl fumarate, monomethyl fumarate, prodrugs thereof, or derivatives thereof. In another embodiment, the lipid or lipophilic vehicle comprises a liquid lipid or lipophilic vehicle comprising oils, fatty acids, fatty acid esters, or a combination thereof. In one embodiment, the vehicle is a single-phase lipid or lipophilic liquid at room temperature and prevents sublimation of the fumarate ester. In another embodiment, the lipid or lipophilic liquid vehicle comprises one or more oils, mono/diglycerides, polyoxyl hydrogenated castor oils, polyvinylpyrrolidones, or a combination thereof. In another embodiment, the lipid or lipophilic liquid vehicle comprises an oil. In another embodiment, the lipid or lipophilic vehicle comprises mono/diglycerides, polyoxyl hydrogenated castor oils, polyvinylpyrrolidones, or a combination thereof.

Exemplary lipid or lipophilic vehicles comprise mineral oil; light mineral oil; natural oils (e.g., vegetable, corn, canola, sunflower, soybean, olive, coconut, cocoa, peanut, almond, cottonseed, persic, sesame, squalane, castor, cod liver) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, or stearyl alcohol, inter alia, or combinations thereof. In one embodiment, the liquid comprises solid particles of fumarate ester suspended in a lipid or lipophilic vehicle of vegetable oil, fatty acid, fatty acid ester, or a combination thereof. In one embodiment, the lipid or lipophilic vehicle is a liquid at room temperature (e.g., 25° C.) or physiological temperature (e.g., 37° C.). In one embodiment, the lipid or lipophilic vehicle is soybean oil. In another embodiment, the lipid or lipophilic vehicle comprises medium chain monoglycerides and diglycerides.

In one embodiment, the composition comprises a solvent or solubility enhancing agent. Exemplary solvents or solubility enhancing agents useful for the compositions described herein include Capmul® MCM, Cremophor® RH 40, Captex® 355, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, or combinations thereof. In one embodiment, the lipid or lipophilic vehicle comprises medium chain mono- and diglycerides (e.g., Capmul® MCM) and polyoxyl 40 hydrogenated castor oil (e.g., macrogolglycerol hydroxystearate; Cremophor® RH 40).

In another embodiment, the composition comprises a one or more hydrophilic solvents or suspension agents. The composition can comprises polyvinylpyrrolidone, polyethylene glycols of molecular weight ranging from about 200 to about 8000 (MN, number average molecular weight), or combinations thereof. In one embodiment, the composition comprises polyvinylpyrrolidone K30 (e.g., Povidone K30). In another embodiment, the composition comprises polyethylene glycol 400 and poly polyvinylpyrrolidone K30.

In another embodiment, the composition comprises a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "*Physical Pharmacy. Physical Chemical Principles in the Pharmaceutical Sciences*," Fourth Edition, pp. 371-373, A. Martin, Ed., Lippincott Williams & Wilkins, Philadelphia (1993), which is incorporated by reference herein for such teachings.

In another embodiment, the composition comprises emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof.

In another embodiment, the composition comprises a neutralizing agent. Without being bound to any theory, the neutralizing agent it thought to stabilize the fumarate ester in the fill by preventing hydrolysis or ester formation with fatty acids. In one aspect, the neutralizing agent comprises an organic acid, ester, or salt. In another aspect, the neutralizing agent comprises an organic acid. In another aspect, the neutralizing agent comprises one or more of lactate, fumarate, caprylate, caprate, oleate, maleate, succinate, tartrate, citrate, glutamate, gluconate, esters or salts thereof, or combinations thereof. In one aspect, the neutralizing agent is lactic acid.

In another embodiment, the composition includes a hydrophilic internal phase and a lipid or lipophilic external phase. The hydrophilic internal phase can comprise polypropylene glycol or polyethylene glycol of molecular weight ranging from about 200 to about 8000 (MN, number average molecular weight). In another embodiment, the internal phase comprises hydroalcoholic solutions of cellulose derivatives, polyacrylates, polyvinyl polymers, or combinations thereof. In one embodiment, the internal phase comprises polymers such as methylcellulose, hydroxypropylmethylcellulose, polymethylmethacrylate, or polyvinylpyrrolidone.

In one embodiment, the internal phase of the composition state is "fluid" or "structured." A "fluid" internal phase, as used herein, means a completely flowable liquid whose globules can aggregate to make a larger globule. A "structured" internal phase, as used herein, means a solid, semisolid, or a gel whose shape is relatively stable and does not usually aggregate to form a large globule. In another embodiment, the external phase comprises a vegetable oil, hydrogenated vegetable oil, fatty acid, fatty acid ester, wax, or a combination thereof. In another embodiment, fumarate ester is dispersed in the internal phase as a solution or suspension.

In one embodiment, the pharmaceutical composition comprises one or more active ingredients comprising one or more fumarate esters. In one embodiment, the pharmaceutical composition comprises a lipid or lipophilic vehicle that provides a solution, suspension, or combination thereof of a fumarate ester. In one embodiment described herein, the fumarate ester is a mono- or di-alkyl fumarate of Formula I:

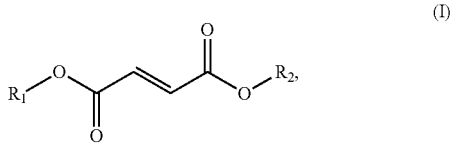

(I)

wherein $R^1$ and $R^2$, which may be the same or different, independently represent hydrogen or a linear, branched, or cyclic, saturated or unsaturated $C_{1-20}$ alkyl radical, which may be optionally substituted with halogen (Cl, F, I, Br), hydroxy, $C_{1-4}$ alkoxy, nitro, or cyano for preparing a pharmaceutical composition as described herein.

The $C_{1-20}$ alkyl radicals, $C_{1-8}$ alkyl radicals, and $C_{4-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. In one aspect, at least one of $R^1$ or $R^2$ is a $C_{1-5}$ alkyl, especially methyl or ethyl. In another aspect, $R^1$ and $R^2$ are the same or different $C_{1-5}$ alkyl radicals such as methyl, ethyl, n-propyl, or t-butyl. In one aspect, $R^1$ and $R^2$ are the same or different $C_{1-5}$ alkyl radicals such as methyl and ethyl. In one aspect, $R^1$ and $R^2$ are identical and are methyl or ethyl. In one aspect, the fumarate ester is monomethyl fumarate, dimethyl fumarate, methyl ethyl fumarate, or diethyl fumarate. In one aspect, the fumarate ester is monomethyl fumarate, dimethyl fumarate, or a combination thereof. In one aspect, the fumarate ester is monomethyl fumarate. In another aspect, the fumarate ester is dimethyl fumarate.

In one embodiment, the fumarate ester is:

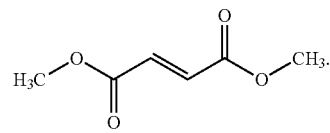

In one embodiment, the fumarate ester is:

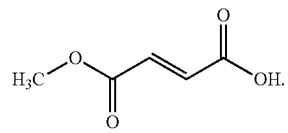

In one embodiment, the fumarate ester is:

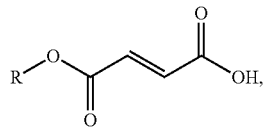

wherein R comprises any $C_{1-20}$ alkyl, any $C_{1-20}$ acid, any $C_{1-20}$ ether, any $C_{1-20}$ ester, any $C_{1-20}$ amino, any $C_{1-20}$ amide, or any $C_{1-20}$ heterocycle.

In another embodiment described herein, the fumarate ester is a prodrug of monomethyl fumarate. In one aspect, the monomethyl fumarate prodrug is dimethyl fumarate. Exemplary monomethyl fumarate prodrugs are described in U.S. Pat. Nos. 8,669,281 and 9,090,558 and U.S. Patent Application Publication Nos. US 2014/0275048; US 2014/0275205; US 2014/0275250; US 2015/0190360; US 2014/057918; US 2014/348914; US 2014/350018; US 2014/056973; US 2014/0348915; and US 2015/0252013, each of which is incorporated by reference herein for such teachings. In one embodiment, the prodrug comprises one or more of N,N-diethylcarbamoyl)methyl methyl(2E)but-2-ene-1,4-dioate; methyl [N-benzylcarbamoyl]methyl (2E)but-2-ene-1,4-dioate; methyl 2-morpholin-4-yl-2-oxoethyl (2E)but-2-ene-1,4-dioate; (N-butylcarbamoyl)methyl methyl(2E)but-2-ene-1,4-dioate; [N-(2-methoxyethyl)carbamoyl]methyl methyl(2E)but-2-ene-1,4-dioate; methyl(N-(1,3,4-thiadiazol-2yl)carbamoyl)methyl(2E)but-2ene-1,4-dioate; (N,N-dimethylcarbamoyl)methyl methyl(2E)but-2-ene-1,4-dioate; (N-methoxy-N-methylcarbamoyl)methyl methyl(2E)but-2-ene-1,4-dioate; bis-(2-methoxyethylamino)carbamoyl]methyl methyl(2E)but-2-ene-1,4-dioate; [N-(methoxycarbonyl)carbamoyl]methyl methyl(2E)but-2ene-1,4-dioate; methyl 2-oxo-2-piperazinylethyl (2E)but-2-ene-1,4-dioate; methyl 2-oxo-2-(2-oxo(1,3-oxazolidin-3yl)ethyl (2E)but-2ene-1,4-dioate; {N-[2-(dimethylamino)ethyl] carbamoyl}methyl methyl(2E)but-2ene-1,4-dioate; ethoxycarbonyloxyethyl methyl (2E)but-2-ene-1,4-dioate; methyl (methylethoxycarbonyloxy)ethyl (2E)but-2-ene-1,4-dioate; (cyclohexyloxycarbonyloxy)ethyl methyl (2E)but-2-ene-1, 4-dioate; methyl (2-methylpropanoyloxy)ethyl (2E)but-2-ene-1,4-dioate; methyl phenylcarbonyloxyethyl (2E)but-2-ene-1,4-dioate; cyclohexylcarbonyloxybutyl methyl (2E) but-2-ene-1,4-dioate; [(2E)-3-(methoxycarbonyl)prop-2-enoyloxy]ethyl methyl (2E)but-2-ene-1,4-dioate; methyl 2-methyl-1-phenylcarbonyloxypropyl (2E)but-2-ene-1,4-dioate; (cyclohexyloxycarbonyloxy)ethyl methyl (2E)but-2-ene-1,4-dioate; 3-({[(2E)-3-(methoxycarbonyl)prop-2-enoyloxy]methyl}oxycarbonyl)(3S)-3-aminopropanoic acid; 3-({[(2E)-3-(methoxycarbonyl)prop-2-enoyloxy] methyl}oxycarbonyl)(2S)-2-aminopropanoic acid; 3-({ [(2E)-3-(methoxycarbonyl)prop-2-enoyloxy] methyl}oxycarbonyl)(3S)-3-(2-aminoacetylamino) propanoic acid; 3-({[(2E)-3-(methoxycarbonyl)prop-2-enoyloxy]methyl}oxycarbonyl)(2S)-2-aminopropanoic acid; 3-{[(2E)-3-(methoxycarbonyl)prop-2enoyloxy] ethoxycarbonyloxy}(2S)-2-aminopropanoic acid; methyl (2-morpholinoethyl)fumarate; methyl (3-morpholinopropyl) fumarate; methyl (4-morpholinobutyl)fumarate; methyl (5-morpholinopentyl)fumarate; methyl (6-morpholinohexyl)fumarate; (E)-2,2'-((2-((4-methoxy-4-oxobut-2-enoyl)oxy)ethyl)azanediyl)diacetic acid; methyl (2-(methyl (2-(methylsulfonyl)ethyl)amino)ethyl)fumarate; 2-(dimethylamino)propyl methyl fumarate; (E)-2-((4-methoxy-4-oxobut-2-enoyl)oxy)-N,N,N-trimethylethanaminium; 2-(4,4-difluoropiperidin-1-yl)ethyl methyl fumarate; 1-(dimethylamino)propan-2-yl methyl fumarate; methyl (2-thiomorpholinoethyl)fumarate; methyl (2-(phenylamino)ethyl)fumarate; 2-(dimethylamino)-2-methylpropyl methyl fumarate; methyl (2-(methylsulfonyl)ethyl)fumarate; 2-(1,1-dioxidothiomorpholino)ethyl methyl fumarate; 2-(benzyl(methyl)amino)ethyl methyl fumarate; 2-(2,5-dioxopyrrolidin-1-yl)ethyl methyl fumarate; methyl (2-(piperidin-1-yl)ethyl)fumarate; methyl (2-morpholinoethyl)fumarate; 2-(1,4-dioxa-8-azaspiro[4.5]decan-8-yl) ethyl methyl fumarate; methyl (2-(pyrrolidin-1-yl)ethyl)fumarate; 2-(dimethylamino)ethyl methyl fumarate; 2-(diethylamino)ethyl methyl fumarate; or 2-(diethylamino)-2-oxoethyl methyl fumarate, or pharmaceutically acceptable salts thereof. In one embodiment, the prodrug is (N,N-diethylcarbamoyl)methyl methyl (2E)but-2-ene-1,4-dioate, or a salt thereof. In another embodiment, the prodrug is 2-(2,5-dioxopyrrolidin-1-yl)ethyl methyl fumarate, or a salt thereof.

In one embodiment, the pharmaceutical compositions described herein comprise pharmaceutically acceptable salts of the fumarate ester active pharmaceutical ingredient. The term "pharmaceutically acceptable salts" of an active ingredient includes alkali metal salts such as, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid, inter alia. In another embodiment, the active ingredient may also be in the form of pharmaceutically acceptable uncharged or charged molecules, molecular complexes, solvates, or anhydrates thereof, and, if relevant, single isomers, enantiomers, racemic mixtures, or mixtures thereof. In another embodiment, the active pharmaceutical ingredient may be in any of its crystalline, polymorphous, semi-crystalline, amorphous, or polyamorphous forms, or mixtures thereof.

In another embodiment, the active ingredient comprises a fumarate ester, combined with aspirin, ibuprofen, naproxene, diclofenac, ketoprofen, celecoxib, other non-steroidal anti-inflamatory active drugs (NSAIDs), or combinations thereof.

In one embodiment, the fumarate ester-to-vehicle ratio range (e.g., the ratio of the fumarate ester weight percent to the weight percent of the other components of the fill or vehicle) comprises from about 1:10 to about 1:1 by mass, including all ratios within the specified range. In one aspect, the fumarate ester-to-vehicle ratio comprises about 1:9 to about 1:1 by mass, including all ratios within the specified range. In another aspect, the fumarate ester-to-vehicle ratio range comprises from about 1:5 to about 1:1 by mass, including all ratios within the specified range. In another aspect, the fumarate ester-to-vehicle ratio range comprises from about 1:2 to about 1:1 by mass, including all ratios within the specified range. In one aspect, the fumarate ester-to-vehicle ratio comprises about 1:2.

In one embodiment, the fumarate ester comprises about 5% to about 75% by mass of the composition, including all integers within the specified range. In another embodiment, the fumarate ester comprises about 10% to about 50% by mass of the composition, including all integers within the specified range. In another embodiment, the fumarate ester comprises about 25% to about 50% by mass of the composition, including all integers within the specified range. In another embodiment, the fumarate ester comprises about 70%; about 60%; about 50%; about 40%; about 35%; about 30%; about 25%; about 20%; about 15%; about 10%; about 5%; about 2%; or about 1% by mass of the composition. In one aspect, the fumarate ester comprises about 34% by mass of the composition.

In one embodiment, the pharmaceutical composition comprises about 25% to about 50% by mass of one or more fumarate esters comprising dimethyl fumarate, monomethyl fumarate, or a combination thereof, and about 50% to about 75% by mass of a lipid or lipophilic vehicle. In one aspect, the composition comprises about 34% by mass of one or more fumarate esters. In another aspect, the lipid or lipophilic vehicle comprises about 66% by mass of the composition. In one aspect, the lipid or lipophilic vehicle comprises a mixture of mono- and di-glycerides, polyvinylpyrrolidone, and polyoxyl 40 hydrogenated castor oil. In another aspect, the lipid or lipophilic vehicle comprises a mixture of mono- and di-glycerides, polyvinylpyrrolidone, polyoxyl 40 hydrogenated castor oil, and lactic acid.

In another embodiment, the pharmaceutical composition comprises about 25% to about 50% by mass of one or more fumarate esters, about 40% to about 54% mass of a mixture of mono- and di-glycerides, about 1% to about 10% by mass of polyvinylpyrrolidone, and about 2% to about 10% by mass of polyoxyl 40 hydrogenated castor oil. In one aspect, the composition further comprises and about 1% to about 5% by mass of lactic acid. In one aspect, the fumarate ester comprises dimethyl fumarate, monomethyl fumarate, or a combination thereof.

In another embodiment, the pharmaceutical composition comprises about 20% to about 50% by mass of one or more fumarate esters, about 18% to about 70% by mass of a mixture of mono- and di-glycerides, about 1% to about 10% by mass polyvinylpyrrolidone, and about 2% to about 12% by mass polyoxyl 40 hydrogenated castor oil. In one aspect, the composition further comprises about 1% to about 5% of lactic acid. In one aspect, the fumarate ester comprises dimethyl fumarate, monomethyl fumarate, or a combination thereof.

In another embodiment, the pharmaceutical composition comprises about 34% by mass of one or more fumarate esters, about 48% by mass of a mixture of mono- and di-glycerides, about 3% by mass polyvinylpyrrolidone, and about 10% by mass polyoxyl 40 hydrogenated castor oil. In one aspect, the composition further comprises about 5% by mass of lactic acid. In one aspect, the fumarate ester comprises dimethyl fumarate, monomethyl fumarate, or a combination thereof.

In one embodiment, the solid fumarate ester particles are milled or micronized. In one aspect, the fumarate ester comprises a particle size range of about 10 μm to about 200 μm, including all integers and fractions within the specified range.

In another embodiment, the solid fumarate ester particles have a particle size distribution with d90 of less than or equal to about 200 km. In one aspect, the solid particles of fumarate ester have a particle size distribution with d90 less than or equal to about 100 μm (d90≤100 km).

In another embodiment, after solubilization or suspension in the liquid compositions described herein the solid fumarate ester particles have a mean particle size distribution comprising a range of particle sizes with d10≤10 km. In another embodiment, the solid fumarate ester particles have a mean particle size distribution comprising a range of particle sizes with d50≤30 km. In another embodiment, the solid fumarate ester particles have a mean particle size distribution comprising a range of particle sizes with d90≤75 km. In one aspect, after solubilization or suspension in the liquid compositions described herein the fumarate ester particles have particle size distributions with d10≤10 km, d50≤30, and d90 of ≤75 km. In another aspect, after solubilization or suspension in the liquid compositions described herein the fumarate ester particles have particle size distributions with d10 of ≤10 km, d50≤25, and d90 of ≤60 km.

The forgoing sizes of fumarate ester particles may be determined using standard techniques known to one of ordinary skill in the art. The exemplary techniques that can be used for measuring the size of fumarate ester particles may include laser diffraction analysis, light scattering (e.g., dynamic light scattering), microscopic particle image analysis, elutriation, or aerosol mass spectrometry. The sample of fumarate ester particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt, following the manufacturer's recommended operating procedures.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter ($D[4,3]$ or $d_{43}$), mean surface area diameter ($D[3,2]$ or $d_{32}$) or the mean number particle diameter ($D[1,0]$ or $d_{10}$). Because the particle size distribution values vary depending on the measurement methodology and how the distribution is expressed, the comparison of different mean particle size distributions must be calculated by the same methodology in order to yield an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

Another embodiment described herein is a method for manufacturing a pharmaceutical composition comprising fumarate ester(s) where the fumarate ester does not sublime during processing, manufacturing, after production, or during storage. Soft capsules comprising fumarate ester in the compositions described herein are stable for months or years. Without being bound to any theory, it is believed that suspending solid fumarate ester particles in a lipid or lipophilic vehicle prevents or retards sublimation and stabilizes the fumarate ester. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, about 18 months, about 24 months, or even longer. In another aspect, the pharmaceutical compositions described herein are stable for at least 1 year, or longer at 25° C. and 60% RH. In another aspect, the pharmaceutical compositions are stable for at least 2 years, or longer at 25° C. and 60% RH.

Another embodiment described herein is a method for preparing a pharmaceutical composition comprising a fumarate ester. The method comprises applying heat to the components during mixing or prior to mixing at about the melting point of the composition; and then mixing the fumarate ester with the ingredients using mechanical or ultrasonic forces to form the matrix fill. The composition is flowable such that it can be encapsulated using a rotary die encapsulation machine. In one embodiment, the composition is heated to a temperature in the range of from about 25° C. to about 70° C. In another embodiment, the composition is heated to a temperature in the range of from about 25° C. to about 30° C.

In one embodiment, the composition comprises a lipid or lipophilic vehicle, solid particles of one or more fumarate esters, neutralizing agent, and optional pharmaceutically acceptable excipients. In one aspect, the composition comprises a mixture of mono- and di-glycerides, polyvinylpyrrolidone, polyoxyl 40 hydrogenated castor oil, lactic acid, and solid particles of one or more fumarate esters. In one aspect, the solid particles of one or more fumarate esters are soluble in the composition. In another aspect, the solid particles of one or more fumarate esters are partially soluble in the composition. Without being bound by any theory, it is believed that the solid particles of fumarate ester dissolve or partially dissolve until the solution becomes saturated and the remaining particle exists as a suspension.

In one embodiment, the composition comprises that shown in Table 1 including all possible iterations of the specified ranges that provide 100% total mass percentage.

TABLE 1

Exemplary Composition

| Component | Mass per capsule (mg) | Mass Percent (%) |
|---|---|---|
| Fumarate Ester | 75-220 | 20-50 |
| Vehicle | 300-500 | 50-80 |
| TOTAL | 500-700 mg | 100% |

In one embodiment, the composition comprises about 34% by mass of fumarate ester (d90≤100 μm); about 50% by mass of a mixture of mono- and di-glycerides; about 3% by mass of polyvinylpyrrolidone; about 10% by mass of polyoxyl 40 hydrogenated castor oil, and about 5% by mass of lactic acid.

In one embodiment, the composition comprises one of those shown in Table 2 including all possible iterations of the specified ranges that provide 100% total mass percentage.

TABLE 2

Exemplary Composition

| Component | Mass per capsule (mg) | Mass Percent (%) |
|---|---|---|
| Fumarate ester (d90 ≤ 100 μm) | 80-200 | 30-35 |
| Mono- and di-glycerides | 125-315 | 20-50 |
| Polyvinyl pyrrolidone | 5-32 | 0.75-5 |
| Polyoxyl 40 hydrogenated castor oil | 12.5-75 | 2-12 |
| Lactic acid | 0-32 | 0-5 |
| TOTAL | 625 mg | 100% |

In one embodiment, the pharmaceutical composition comprises a capsule dosage form. In one embodiment, the pharmaceutical composition comprises a soft capsule encapsulating a matrix fill comprising a liquid lipid or lipophilic fill comprising one or more fumarate esters.

In one embodiment described herein, the soft capsule shell has the exemplary composition shown in Table 4.

TABLE 3

Exemplary Soft Capsule Shell Composition

| Component | Mass Percent (%) |
|---|---|
| Film forming polymer (e.g., gelatin) | 20-50 |
| Plasticizer (e.g., glycerol, sorbitol, combinations thereof) | 15-30 |
| Solvent (e.g., water) | q.s. (e.g., 20-40%) |
| TOTAL | 100% |
| Final pH | ~4-7 |
| Ratio total plasticizer to gelatin | 20:43 (0.46:1) |
| Water content in dried soft capsule shell: | 8-15% |

In one embodiment, the soft capsule comprises about 42% of gelatin; about 24% of at least one plasticizer; and about 34% water.

In another embodiment, the soft capsule shell has the exemplary composition shown in Table 4.

TABLE 4

Exemplary Soft Gel Capsule Shell Composition

| Component | Mass Percent (%) |
|---|---|
| Gelatin, 195 Bloom, Lime Bone | 42 |
| Sorbitol (e.g., Polysorb ® 85/70/00; Roquette) | 24 |
| Water | 34 |
| TOTAL | 100% |

Another embodiment described herein includes a process of manufacturing soft capsules comprising any of the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm). In another embodiment, the shell thickness is about 0.035 inches (≈0.889 mm). In another embodiment, the shell thickness is about 0.038 inches (≈0.965 mm). In another embodiment, the shell thickness is about 0.040 inches (≈1.02 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In one embodiment described herein, soft capsules are coated with an enteric coating comprising the exemplary composition shown in Table 5.

TABLE 5

Exemplary Enteric Coating Composition

| Component | Exemplary Component | Mass Percent (%) |
|---|---|---|
| Enteric Polymer(s) | Methacrylic acid copolymers, polyvinyl acetate phthalates, polyvinyl phthalate, cellulose acetate phthalates, cellulose acetate trimellitate, cellulose acetate succinate, hydroxypropyl methylcellulose, carboxymethyl cellulose | 5-90 |
| Plasticizer(s) | Triethyl citrate, tributyl citrate, polyethylene glycols, propylene glycol, triacetin, dibutyl phthalate, tripropionin, ethyl acid phtalate, butyl acid phthalate, ethyl acid adipate, fats and waxes mixed with esters, glycerin | 0-25 |
| Neutralizing agent | Ammonia, NaOH, sodium bicarbonate | 0-5 |
| Solubilizers | Sodium lauryl sulfate, sodium lauroyl sarcosinate sodium dodecyl sulfate, polysorbate 20, polysorbate 80, other detergents and surfactants | |
| Solvent(s) | Water, ethanol, isopropanol, acetone | 50-80 |
| Excipients | Emulsifiers, pore-forming agents, anti-adherents, surfactants, pigments, colorants, antifoam, antioxidants, waxes, magnesium stearate, micronized amorphous silica, kaolin, talc, | 0-20 |
| TOTAL | | 100% |

Enteric polymers useful for enteric coatings include pH-dependent polymers that are less soluble in an aqueous media with acidic pH and more soluble in an aqueous media with basic pH. In one embodiment, the enteric of pH dependent material dissolves or rapidly disperses at a pH level above pH 5.0, above pH 5.5, or above pH 6.0.

Exemplary enteric polymers useful for coats include cellulose acetate phthalate, hydroxypropylmethyl cellulose phthalate, hydroxypropyl methylcellulose acetate succinate, polyvinyl acetate phthalate, cellulose acetate trimellitate, carboxymethylcellulose, methacrylic acid copolymers such as, Eudragit L (polymethacrylic acid, methylmethacrylate, 1:1 ratio), or Eudragit S (polymethacrylic acid, methylmethacrylate, 1:2 ratio), shellac, zein, or combinations thereof.

Suitable plasticizers include acetyl triethyl citrate, dibutyl phthalate, tributyl citrate, triethyl citrate, acetyl tributyl citrate, propylene glycol, triacetin, polyethylene glycol, diethyl phthalate, or combinations thereof.

Suitable solubilizers include sodium lauryl sulfate, sodium lauryl sarcosinate, sodium dodecyl sulfate, polysorbate 20, polysorbate 80, octylphenoxy polyethoxyethanol, or combinations thereof.

Anti-adherent agents serve to prevent potential agglomeration in acid media. Suitable anti-adherents include talc, magnesium stearate, calcium stearate, stearic acid, hydrogenated vegetable oils, polyethylene glycols, fumed silica, silicon dioxide, or combinations thereof.

Pore-forming agents serve to create pores or channels in the enteric coating after administration to a human. Suitable pore-forming agents include sodium chloride, potassium chloride, sucrose, sorbitol, mannitol, polyethylene glycols (PEG), propylene glycol, hydroxypropyl cellulose, hydroxypropyl methylcellulose, polyvinyl alcohols, methacrylic acid copolymers, poloxamers, or combinations thereof.

Many conventional coating excipients are described in the art. See e.g., Rowe et al., Eds. *Handbook of Pharmaceutical Excipients*, $7^{th}$ ed. Royal Pharmaceutical Society, UK (2012).

In one embodiment described herein, the enteric coating comprises methacrylic acid and ethyl acrylate copolymer (e.g., EUDRAGIT® L100-55, Evonik), talc, triethyl citrate, sodium bicarbonate, colloidal silica, sodium lauryl sulfate, and water.

In one embodiment, adjusting the amount of enteric coating and the ratio of polymer to other components allows for tuning the release profile of the dosage form.

Subcoats can be applied to the soft capsules prior to coating to prevent shell-coat interactions and improve coating adhesion to the capsule. Exemplary subcoatings can comprise polyvinylpyrrolidone, polyvinyl alcohols, hydroxypropyl methylcellulose, polyethylene glycol, oils, or combinations thereof.

Coatings, top coatings, or subcoatings are applied to the soft capsules using various methods know in the art. The coatings are typically prepared as suspensions and sprayed on capsules in perforated coating pans through one or more spray nozzles at a specific temperature. Coating solutions or dispersion may be applied at spray rates between 100 and 400 g/min. The spray rate may be proportionally higher for coatings with higher solids content and lower for more dilute dispersions. In one embodiment, capsules are coated using a pan coater. After the enteric coating suspension is applied, the coated capsules are dried in the pan coater for a period of time at a specific temperature.

Another embodiment described herein comprises a subcoating that is applied prior to applying an enteric coating. In one embodiment, the subcoating comprises hydroxypropyl methylcellulose, methylcellulose, ethylcellulose, or a combination thereof. In one aspect, the subcoating comprises hydroxypropyl methylcellulose.

Another embodiment described herein comprises a moisture barrier that is applied as a top coating on the enteric coating. In one embodiment, the moisture barrier comprises one or more polyvinyl alcohols and appropriate pharmaceutically acceptable excipients. In another embodiment, the moisture barrier comprises polyvinyl alcohol, sodium lauryl sulfate, glyceryl mono-caprylate-caprate, and talc. In one aspect, the moisture barrier aids in preserving the cosmetic appearance of the dosage forms by preventing dimpling, sticking, or other processing- or storage-induced blemishes.

Another embodiment described herein, is a pharmaceutical composition comprising a matrix fill formulation comprising any of the formulations shown in the Tables or Examples described herein. Any of the components in the formulations described herein, shown in the Tables, or illustrated in the Examples can be increased, decreased, combined, substituted, or omitted to provide for a formulation comprising about 100% by mass. Such compositions are hereby disclosed as if they were expressly disclosed herein.

In one embodiment, the pharmaceutical compositions described herein provide a dosage form of one or more fumarate esters, or prodrugs thereof, for administration to a subject. In one embodiment, the subject is suffering from or has the symptoms of multiple sclerosis or a neurological disease or disorder. The dosage form can be administered, for example, to a subject, or a subject in need thereof. In one aspect, the subject is a mammal, or a mammal in need thereof. In one aspect, the subject is a human, or human in need thereof. In one aspect, the subject is a human. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (≥18 years of age).

One or more dosage forms can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, general autoimmune or neurodegenerative disorders.

Another embodiment described herein is a method of treating a subject suffering from or having the symptoms of a general autoimmune or neurodegenerative disorder, including multiple sclerosis, by orally administering one or more fumarate esters to the subject. The one or more fumarate esters may be administered in one or more doses, one or more times per day for a total daily dosage.

In one embodiment, the pharmaceutical composition described herein is administered in multiple doses simultaneously. For example, two or more identical doses are administered at one time. In another embodiment, two or more different doses are administered at one time. Such dual or different simultaneous doses can be used to provide an effective amount of the pharmaceutical composition to a subject in need thereof.

In another embodiment, the pharmaceutical compositions described herein may be used to treat, prevent, retard the progression of, delay the onset, ameliorate, reduce the symptoms of, or prophylaxis of general autoimmune or neurodegenerative disorders. Neurodegenerative disorders, as used herein, include multiple sclerosis (MS), which includes relapsing remitting multiple sclerosis (RRMS), secondary progressive multiple sclerosis (SPMS), primary progressive multiple sclerosis (PPMS), progressive relapsing multiple sclerosis (PPvMS), amyotrophic lateral sclerosis (ALS), psoriasis, psoriatic arthritis, Alzheimer's disease, Parkinson's disease, or any combination thereof.

In one embodiment described herein, other conditions, disorders, or diseases are controlled by administration of fumarate esters. The administration of pharmaceutical compositions comprising fumarate esters, as described herein, may be used for treating, preventing, retarding the progression of, delaying the onset, ameliorating, reducing the symptoms of, or prophylaxis of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behcet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radiation-induced dermatitis, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome.

In one embodiment, the pharmaceutical compositions described herein are indicated for the treatment of patients with relapsing forms of multiple sclerosis. Another embodiment described herein is a method for treating a patient with a relapsing form of multiple sclerosis comprising the administration of one or more doses of a fumarate ester as described herein. In one aspect, the fumarate ester is dimethyl fumarate, monomethyl fumarate, a prodrug of monomethyl fumarate, or combinations thereof.

Another embodiment described herein is a pharmaceutical composition comprising an oral delayed-release capsule of dimethyl fumarate that is indicated for the treatment of patients with relapsing forms of multiple sclerosis. Another embodiment described herein is a pharmaceutical composition comprising an oral delayed-release capsule of monomethyl fumarate that is indicated for the treatment of patients with relapsing forms of multiple sclerosis. Another embodiment described herein is a pharmaceutical composition comprising an oral delayed-release capsule of dimethyl fumarate, monomethyl fumarate, or a combination thereof that is indicated for the treatment of patients with relapsing forms of multiple sclerosis. Another embodiment described herein is a pharmaceutical composition comprising an oral delayed-release capsule of a pro-drug of monomethyl fumarate that is indicated for the treatment of patients with relapsing forms of multiple sclerosis.

In one embodiment, the pharmaceutical composition comprises a dose of about 60 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, or about 230 mg of one or more fumarate esters. In one aspect, the fumarate ester is dimethyl fumarate, monomethyl fumarate, a pro-drug of monomethyl fumarate, or a combination thereof.

In another embodiment, the composition comprises a dose of about 60 mg to about 80 mg, about 65 mg to about 85 mg, about 70 mg to about 90 mg, about 75 mg to about 95 mg, about 80 mg to about 100 mg, about 85 mg to about 105 mg, about 90 mg to about 110 mg, about 95 mg to about 115 mg, about 100 mg to about 120 mg, about 105 mg to about 125 mg, about 110 mg to about 130 mg, about 115 mg to about 135 mg, about 120 mg to about 140 mg, about 125 mg to about 145 mg, about 130 mg to about 150 mg, about 135 mg to about 155 mg, about 140 mg to about 160 mg, about 145 mg to about 165 mg, about 150 mg to about 170 mg, about 155 mg to about 175 mg, about 160 mg to about 180 mg, about 165 mg to about 185 mg, about 170 mg to about 190 mg, about 175 mg to about 195 mg, about 180 mg to about 200 mg, about 185 mg to about 205 mg, about 190 mg to about 210 mg, about 195 mg to about 215 mg, about 200 mg to about 220 mg, about 205 mg to about 225 mg, about 210 mg to about 230 mg, about 215 mg to about 235 mg, about 220 mg to about 240 mg, about 225 mg to about 245 mg, about 230 mg to about 250 mg, or about 230 mg to about 250 mg of one or more fumarate esters.

In one embodiment, the foregoing compositions can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage. In another embodiment, any of the foregoing doses may be administered simultaneously, such as two 75 mg, 85 mg, 95 mg, or two 100 mg fumarate ester dosage forms, to provide 150 mg, 160 mg, 190 mg, or 200 mg fumarate ester for a particular dosing period, typically a 24 hour period, or 1 day.

Without being bound by any theory, it is thought that simultaneously administering two or more dosage forms, such as two 75 mg, 80 mg, 85 mg, 90 mg, 95 mg or 100 mg fumarate ester dosage forms (e.g., total fill weight of about 250 to about 300 mg in a No. 5 oval capsule) provides more rapid gastric emptying and transit to the duodenum as compared to a single larger dosage form, such as a single 200 mg fumarate ester dosage form (e.g., total fill weight of about 500 mg to about 600 mg in a No. 12 oval capsule). This regimen may provide a more rapid $T_{max}$ and also reduce $C_{max}$ because of the lower fumarate ester dose. This regimen may also reduce gastrointestinal side effects.

In another embodiment, one or more dosage forms are administered simultaneously or successively over a finite period (such as 1 hour) to provide a dose comprising about 60 mg to about 120 mg, about 65 mg to about 130 mg, about 70 mg to about 140 mg, about 75 mg to about 150 mg, about 80 mg to about 160 mg, about 85 mg to about 170 mg, about 90 mg to about 180 mg, about 95 mg to about 190 mg, about 100 mg to about 200 mg, about 105 mg to about 210 mg, about 110 mg to about 220 mg, about 115 mg to about 230 mg, about 120 mg to about 240 mg, about 125 mg to about 250 mg, about 130 mg to about 260 mg, about 135 mg to about 270 mg, about 140 mg to about 280 mg, about 145 mg to about 290 mg, about 150 mg to about 300 mg, about 155 mg to about 310 mg, about 160 mg to about 320 mg, about 165 mg to about 330 mg, about 170 mg to about 340 mg, about 175 mg to about 350 mg, about 180 mg to about 360 mg, about 185 mg to about 370 mg, about 190 mg to about 380 mg, about 195 mg to about 390 mg, about 200 mg to about 400 mg, about 205 mg to about 410 mg, about 210 mg to about 420 mg, about 215 mg to about 430 mg, about 220 mg to about 440 mg, about 225 mg to about 450 mg, about 230 mg to about 460 mg, or about 230 mg to about 460 mg of one or more fumarate esters.

In another embodiment, one or more dosage forms are administered simultaneously or successively in a finite period to provide a dose comprising about 60 mg to about 180 mg, about 65 mg to about 195 mg, about 70 mg to about 210 mg, about 75 mg to about 225 mg, about 80 mg to about 240 mg, about 85 mg to about 255 mg, about 90 mg to about 270 mg, about 95 mg to about 285 mg, about 100 mg to about 300 mg, about 105 mg to about 315 mg, about 110 mg to about 330 mg, about 115 mg to about 345 mg, or about 120 mg to about 360 mg of one or more fumarate esters.

In another embodiment, one or more dosage forms are administered simultaneously or successively in a finite period multiple time per day to achieve a daily dosage. In one embodiment, the total daily dosage is about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, or about 460 mg of one or more fumarate esters.

In another embodiment, the daily dosage is about 60 mg to about 240 mg, about 65 mg to about 260 mg, about 70 mg to about 280 mg, about 75 mg to about 300 mg, about 80 mg to about 320 mg, about 85 mg to about 340 mg, about 90 mg to about 360 mg, about 95 mg to about 380 mg, about 100 mg to about 400 mg, about 105 mg to about 420 mg, about 110 mg to about 440 mg, about 115 mg to about 460 mg, or about 120 mg to about 480 mg of one or more fumarate esters.

Another embodiment described herein is a method of treating a subject having relapsing forms of multiple sclerosis with one or more dosage forms having a specific dose of fumarate ester. In one aspect, the subject is orally administered one or more pharmaceutical dosage forms as described herein comprising a dose of about 60 mg to about 90 mg of a fumarate ester comprising dimethyl fumarate, monomethyl fumarate, a prodrug of monomethyl fumarate, or a combination thereof twice per day for about seven days. In one aspect, the subject is orally administered one or more pharmaceutical dosage forms as described herein comprising a dose of about 70 mg to about 95 mg of a fumarate ester comprising dimethyl fumarate, monomethyl fumarate, a prodrug of monomethyl fumarate, or a combination thereof twice per day for about seven days. In one aspect, the subject is orally administered one or more pharmaceutical dosage forms as described herein comprising a dose of about 80 mg to about 100 mg of a fumarate ester comprising dimethyl fumarate, monomethyl fumarate, a prodrug of monomethyl fumarate, or a combination thereof twice per day for about seven days.

Another embodiment described herein is a method of treating a subject having relapsing forms of multiple sclerosis with one or more dosage forms having a specific dose of fumarate ester to achieve a total daily dose. In another aspect, the subject is orally administered one or more pharmaceutical dosage forms as described herein comprising a total dose of about 120 to about 180 mg of a fumarate ester comprising dimethyl fumarate, monomethyl fumarate, a prodrug of monomethyl fumarate, or a combination thereof twice per day. In another aspect, the subject is orally administered one or more pharmaceutical dosage forms as described herein comprising a total dose of about 140 to about 190 mg of a fumarate ester comprising dimethyl fumarate, monomethyl fumarate, a prodrug of monomethyl fumarate, or a combination thereof twice per day. In another aspect, the subject is orally administered one or more pharmaceutical dosage forms as described herein comprising a total dose of about 160 to about 200 mg of a fumarate ester comprising dimethyl fumarate, monomethyl fumarate, a prodrug of monomethyl fumarate, or a combination thereof twice per day. In another aspect, the subject is orally administered two pharmaceutical dosage forms as described herein each comprising a dose of about 80 mg to about 100 mg, comprising a total dosage of about 160 to 200 mg, of a fumarate ester comprising dimethyl fumarate, monomethyl fumarate, a prodrug of monomethyl fumarate, or a combination thereof twice per day.

Another embodiment described herein is a pharmaceutical dosage form comprising a pharmaceutical composition as described herein for administration to a subject having multiple sclerosis, comprising a therapeutically effective amount of one or more fumarate esters, wherein the administration is sufficient to achieve a reduction of about 0.224 annualized relapse rate relative to baseline in the subject. In one aspect, the fumarate ester comprises dimethyl fumarate, monomethyl fumarate, a prodrug of monomethyl fumarate, or a combination thereof. In another aspect, the pharmaceutical composition treats multiple sclerosis without substantially inducing one or more of flushing, abdominal pain, diarrhea, and nausea in the subject. In another aspect, the administration does not require titration of the pharmaceutical composition. In another aspect, the dosage form is stable at 25° C. and 60% relative humidity for at least 1 year or 2 years.

In one embodiment described herein, without being bound to any theory, it is surprising and unexpected that the pharmaceutical compositions described herein comprising liquid dosage forms of fumarate ester provide effective treatment of multiple sclerosis at total daily dosages of about 380 mg fumarate ester to about 400 mg fumarate ester when compared to a total daily dosage of 480 mg dimethyl fumarate administered as TECFIDERA®. In one embodiment, the fumarate ester is dimethyl fumarate. In another embodiment, the fumarate ester is monomethyl fumarate. In another embodiment, the fumarate ester is a pro-drug of monomethyl fumarate. In another embodiment, the fumarate ester is monomethyl fumarate. In another embodiment, the fumarate ester is dimethyl fumarate, monomethyl fumarate, a prodrug of monomethyl fumarate, or a combination thereof.

Another embodiment described herein is a pharmaceutical dosage form that has improved bioavailability as compared to another pharmaceutical product. In one aspect, the pharmaceutical dosage form comprising the pharmaceutical composition described herein has improved bioavailability as compared to 240 mg dimethyl fumarate administered as TECFIDERA®. In one aspect, two pharmaceutical dosage forms, each comprising about 80 mg to about 100 mg of dimethyl fumarate, monomethyl fumarate, or a combination thereof, administered to a subject has equivalent pharmacokinetics as one 240 mg dimethyl fumarate dosage form (e.g., TECFIDERA®).

In one embodiment, the pharmaceutical compositions and dosage forms described herein can be administered without titration of the pharmaceutical composition. In one aspect, the pharmaceutical compositions and dosage forms can be administered without titration and without substantially inducing one or more side effects including, but not limited to flushing, abdominal pain, diarrhea, or nausea.

Prior to beginning treatment with the pharmaceutical compositions and dosage forms described herein, a complete blood cell count (CBC) including lymphocyte count, and serum aminotransferase, alkaline phosphatase, and total bilirubin levels should be obtained from the subject in need of treatment.

Fumarate esters can cause flushing and gastrointestinal (GI) side effects in some subjects. While the side effects generally subside after regular treatment, in one aspect the starting dose is about 80 mg to about 100 mg fumarate ester BID orally for the first 7 days. The dose is increased to the effective dose of about 160 mg to about 200 mg fumarate ester BID (e.g., about 320 mg to about 400 mg fumarate ester per day) afterwards. For those subjects who experience GI or flushing side effects, taking the fumarate ester with food can improve tolerability. In one aspect described herein, fumarate ester is administered after a meal. In another aspect described herein, fumarate ester is administered after a high-fat meal to reduce or ameliorate the one or more symptoms of flushing, abdominal pain, diarrhea, and nausea in the subject. In another aspect, about 325 mg of non-enterically coated aspirin or about 200 mg to 400 mg of other NSAID, including acetaminophen, ibuprofen, naproxen, diclofenac, salts thereof, or combinations thereof are administered about 0.5 h prior to administration of the fumarate ester composition or dosage form as described herein.

In one aspect, the administration of about 325 mg of non-enteric coated aspirin 30 minutes prior to fumarate ester dosing can reduce the occurrence and severity of flushing. In another aspect, subjects who experience flushing with gastrointestinal side effects may reduce the dose to about 80 mg to about 100 mg fumarate ester BID temporarily, including all integers and fractions within the specified range. Within a month, the effective dose of about 160 mg to about 200 mg fumarate ester BID should be resumed, including all integers within the specified range.

In another embodiment, a subject administered a fumarate ester pharmaceutical composition described herein may be administered one or more leukotriene receptor antagonists. In one embodiment, a subject administered a fumarate ester pharmaceutical composition as described herein may be administered 10 to 20 mg of montelukast (Singulair®) or zafirlukast (Accolate®) in conjunction with the fumarate ester.

Another embodiment described herein is a pharmaceutical dosage form that provides delayed release of one or more fumarate esters. In one aspect, the dosage form comprises a soft capsule encapsulating an immediate releasing fill. In another aspect, the pharmaceutical dosage from comprises a fumarate ester, a mixture of mono- and di-glycerides, polyvinylpyrrolidone, polyoxyl 40 hydrogenated castor oil, and lactic acid encapsulated in an soft capsule shell that is coated with a hydroxypropylmethylcellulose coating, a methacrylic acid and ethyl acrylate copolymer, and a polyvinyl alcohol coating. In another aspect, the pharmaceutical dosage form is stable at pH 1.2 for at least 2 hours in an in vitro 2-stage dissolution experiment comprising a USP Apparatus II (e.g., stationary basket over paddle at 100 rpm in 900 mL of media, 37° C.). In another aspect, the pharmaceutical dosage form begins releasing the fill after about 15 minutes at pH 6.8 in an in vitro 2-stage dissolution experiment comprising a USP Apparatus 2 (e.g., stationary basket over paddle at 100 rpm in 900 mL of media, 37° C.). See USP Reference Standard Method ⟨711⟩ Dissolution, which is incorporated by reference for such teachings. In one aspect, the pharmaceutical dosage form releases about 50% of the fill composition after about 52 minutes at pH 6.8. In one aspect, the pharmaceutical dosage form releases about 50% of the fill composition after about 64 minutes at pH 6.8. In one aspect, the pharmaceutical dosage form releases about 48 mg of the fumarate ester after about 52 minutes at pH 6.8. In one aspect, the pharmaceutical dosage form releases about 100 mg of fumarate ester after about 64 minutes at pH 6.8.

Another embodiment described herein is a pharmaceutical dosage form comprising about 190 mg of dimethyl fumarate, monomethyl fumarate, or a combination thereof in a single phase lipid or lipophilic liquid encapsulated in capsule, where upon administration the dosage from provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\% \ ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a pharmaceutical dosage form comprising about 200 mg of dimethyl fumarate, monomethyl fumarate, or a combination thereof in a single phase lipid or lipophilic liquid encapsulated in capsule, where upon administration the dosage from provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr·ng/mL; (e) a mean plasma monomethyl fumarate $AUC_{\% \ ex}$ of about 0.86%; (f) a mean plasma monomethyl fumarate $K_{el}$ of about 1.4 hr$^{-1}$; or (g) a mean plasma monomethyl fumarate $t_{1/2}$ of about 0.5 hr.

Another aspect is one or more pharmaceutical dosage forms, collectively comprising about 160 mg to about 190 mg of dimethyl fumarate, monomethyl fumarate, or a combination thereof in a single-phase lipid or lipophilic liquid encapsulated in capsule, where upon administration the total dose is bioequivalent to 240 mg of dimethyl fumarate (TECFIDERA®). In one aspect, the pharmaceutical dose comprises one capsule. In another aspect, the pharmaceutical dose comprises more than one capsule.

Pharmacokinetics of fumarate esters, particularly dimethyl fumarate, are described by Sheikh et al., *Clinical Therapeutics* 35(10): 1582-1594 (2013), which is incorporated by reference herein for such teachings. Dimethyl fumarate is not quantifiable in plasma following oral administration. After ingestion, dimethyl fumarate is pre-systemically hydrolyzed by esterases and is converted to the active metabolite, monomethyl fumarate (MMF). All pharmacokinetic analyses related to DMF are performed using plasma MMF concentrations because DMF is converted to MMF and DMF is not quantifiable in systemic circulation. If monomethyl fumarate is orally administered, the MMF concentration can be directly measured in plasma.

Another embodiment described herein is a method for treating or reducing the symptoms of a neurodegenerative disorder, including multiple sclerosis, comprising administering to a subject in need thereof one or more of the dosage forms described herein comprising about 190 mg of dimethyl fumarate, monomethyl fumarate, or a combination thereof, where upon administration the dosage from provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\% \ ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

Another embodiment described herein is a method for treating or reducing the symptoms of a neurodegenerative disorder, including multiple sclerosis, comprising administering to a subject in need thereof one or more of the dosage forms described herein comprising about 200 mg of dimethyl fumarate, monomethyl fumarate, or a combination thereof, where upon administration the dosage from provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr·ng/mL; (e) a mean plasma monomethyl fumarate $AUC_{\% \ ex}$ of about 0.86%; (f) a mean plasma monomethyl fumarate $K_{el}$ of about 1.4 hr$^{-1}$; or (g) a mean plasma monomethyl fumarate $t_{1/2}$ of about 0.5 hr.

Another aspect is a method for treating or reducing the symptoms of a neurodegenerative disorder, including multiple sclerosis, comprising administering to a subject in need thereof one or more of the dosage forms described herein comprising about 160 mg to about 190 mg of dimethyl fumarate, monomethyl fumarate, or a combination thereof, where upon administration the dose is bioequivalent to 240 mg of dimethyl fumarate (TECFIDERA®).

Another embodiment described herein is a method for manufacturing an oral pharmaceutical composition comprising the steps of:
(a) introducing mono- and di-glycerides into a 200 L mixing vessel, adding polyvinylpyrrolidone, and mixing at 400±200 rpm at 60±5° C. for not less than 30 min until the solution is clear;
(b) adding polyoxyl 40 hydrogenated castor oil and mixing the solution at 400±200 rpm at 60±5° C. for not less than 30 min until the solution is clear;
(c) adding lactic acid and mixing at 400±200 rpm at 60±5° C. for not less than 30 min until uniformly blended;
(d) cooling the solution in 200 L tank to 25±5° C. while mixing at 400±200 rpm (a placebo fill can be removed at this step);
(e) vacuum transferring the solution to a 500 L vacuum deaerator at 20±5° C. and mixing under vacuum for no less than 5 min;
(f) introducing solid particles of the fumarate ester API (PSD: 40-150 μm) into the deaerator vessel and homogenizing the suspension for no less than 15 min;
(g) vacuum transferring the suspension to a 200 L medicine tank and deaerating no less than 30 min at 20±5° C.; and
(h) homogenizing to form a final suspension at 10-50 rpm.

When the pharmaceutical composition is encapsulated in a soft capsule, the following steps are included:
(i) preparing a gel mass composition comprising a film-forming, water-soluble polymer, an appropriate plasticizer, and solvent;
(j) casting the gel mass into films or ribbons using heat-controlled drums or surfaces;
(k) transferring the homogenized suspension of step (h) to an encapsulation line;

(l) injecting and encapsulating the transferred homogenized fill solution (k) within the gel mass films or ribbons using rotary dye encapsulation to create a capsule;

(m) drying and finishing the capsules;

(n) optionally, coating capsules with a sub-coating and drying;

(o) optionally, coating capsules with a coating and drying;

(p) optionally, coating capsules with a top coating and drying; and (q) post processing and packaging.

In one aspect, the coatings of steps (n)-(p) are performed in a coating pan. In another aspect, the subcoating of step (n) comprises hydroxypropylmethylcellulose. In another aspect, the coating of step (o) comprises an enteric coating. In another aspect, the coating of step (o) comprises an enteric coating comprising a methacrylic acid and ethyl acrylate copolymer. In another aspect, the coating of step (o) comprises a polyvinyl alcohol coating.

Another embodiment described herein is a method for treating a neurological disease, neurodegenerative disease, autoimmune disease, or an iatrogenic disease or disorder comprising orally administering one or more doses of one or more fumarate esters described herein to a patient in need thereof, wherein the administration activates or modulates one or more cellular signaling pathways. In one aspect, the cellular signaling pathway comprises the nuclear erythroid-derived 2-like 2 (Nrf2) dependent antioxidant response element (ARE) pathway. Without being bound by any theory, it is believed that at least one aspect of the pharmacological activity of the fumarate esters described herein exert an anti-inflammatory and neuroprotective effect in patients with, for example, multiple sclerosis or psoriasis, by activating the Nrf2 cellular signaling pathway. Although not completely understood, the Nrf2 pathway is involved in the cellular response to oxidative stress, which has been linked to neuronal degeneration in multiple sclerosis and in other neurodegenerative or autoimmune diseases (e.g., HIV), see, e.g., Gao et al., *Clin. Pharmacol.* 6:19-34 (2014), which is incorporated by reference herein for its teachings thereof.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Two formulations of soft capsules comprising particles of a fumarate ester having particle size distributions of PSD: d90≤100 μm were manufactured. The dosage forms comprised two doses of fumarate ester, all with the same fill composition and the same soft gelatin shell. The doses were either 95 mg or 200 mg, fumarate ester and comprised 34% fumarate ester, 48% of a mixture of mono- and di-glycerides (e.g., Capmul® MCM), 3% polyvinylpyrrolidone, 10% polyoxyl 40 hydrogenated castor oil, and 5% lactic acid. See Table 6. The matrix fill was encapsulated in soft gelatin capsules comprising 195 Bloom gelatin using rotary die encapsulation. See Table 7. The 90 mg dosage form was manufactured as number 5 oval capsules and the 200 mg dosage form was manufactured as number 12 oval capsules. After manufacturing and drying, the capsules were coated with a hydroxypropylmethylcellulose undercoat and dried. The capsules were then coated with an enteric coating containing methacrylic acid, ethyl acrylate copolymer (e.g., EUDRAGIT® L100-55, Evonik; Acryl-EZE®, Colorcon). See Table 8. A polyvinyl alcohol moisture barrier topcoating was applied to the enterically coated capsules (e.g., Opadry® amb II, Clear, Colorcon). Table 9.

TABLE 6

Fumarate Ester Compositions

| Component | 95 mg Dose | | 200 mg Dose | |
|---|---|---|---|---|
| | Mass (mg) | Mass % | Mass (mg) | Mass % |
| Fumarate Ester | 95 | 34.2 | 200 | 34.2 |
| Capmul MCM | 132.5 | 47.8 | 278.9 | 47.8 |
| Povidone K30 | 8.3 | 3.0 | 17.5 | 3.0 |
| Polyoxyl 40 hydrogenated castor oil | 27.7 | 10.0 | 58.4 | 10.0 |
| Lactic Acid | 13.9 | 5.0 | 29.2 | 5.0 |
| TOTAL | 277.4 | 100.0% | 584 | 100.0% |
| Relational Mases and Ratios | Mass (mg) | Mass % | Mass (mg) | Mass % |
| Vehicle Mass | 182.4 | 66 | 384 | 66 |
| Lipid Mass | 168.5 | 61 | 354.8 | 61 |
| API Mass | 95 | 34 | 200 | 34 |
| Mass Ratio API:Lipid | 0.56 | 0.56 | 0.56 | 0.56 |
| Mass Ratio API:Vehicle | 0.52 | 0.52 | 0.52 | 0.52 |

TABLE 7

Exemplary Soft Capsule Shell Composition

| Component | Mass (g) | Mass Percent (%) |
|---|---|---|
| Gelatin, 195 Bloom | 172.4 | 52.2 |
| Polysorb ® 85/70/00 (D-Sorbitol/sorbitans) | 99.0 | 30.0 |
| Purified water | 58.0 | 17.6 |
| Titanium Dioxide | 0.8 | 0.24 |
| FD&C Blue # 1 | 0.2 | 0.06 |
| TOTAL | 330.4 | 100.0% |

TABLE 8

Exemplary Enteric Coating Composition (Acryl-EZE ®, Colorcon)

| Component | Mass (g) | Mass Percent (%) |
|---|---|---|
| Methacrylic acid, ethyl acrylate copolymer | | |
| Talc | | |
| Triethyl citrate | 1896 | 86.6 |
| Sodium bicarbonate | | |
| Colloidal anhydrous silica | | |
| Sodium lauryl sulfate | | |
| Triethyl citrate* | 233.8 | 11.4 |
| Water† | 8236 | 399.8 |
| TOTAL | 2059.8 | 100.0% |

*Additional triethyl citrate added.

†A majority of the water evaporates during the coating process.

TABLE 9

Moisture Barrier Top Coating Composition (Opadry ® amb II, Clear; Colorcon)

| Component | Mass (g) | Mass Percent (%) |
|---|---|---|
| Polyvinyl alcohol | | |
| Glyceryl mono-caprylate-caprate | | |
| Sodium lauryl sulfate | 600 | 10.0 |
| Talc | | |
| Titanium Dioxide | | |
| Water* | 5400 | 90.0 |
| TOTAL | 6000 | 100.0% |

*A majority of the water evaporates during the coating process.

Example 2

Figure 2:
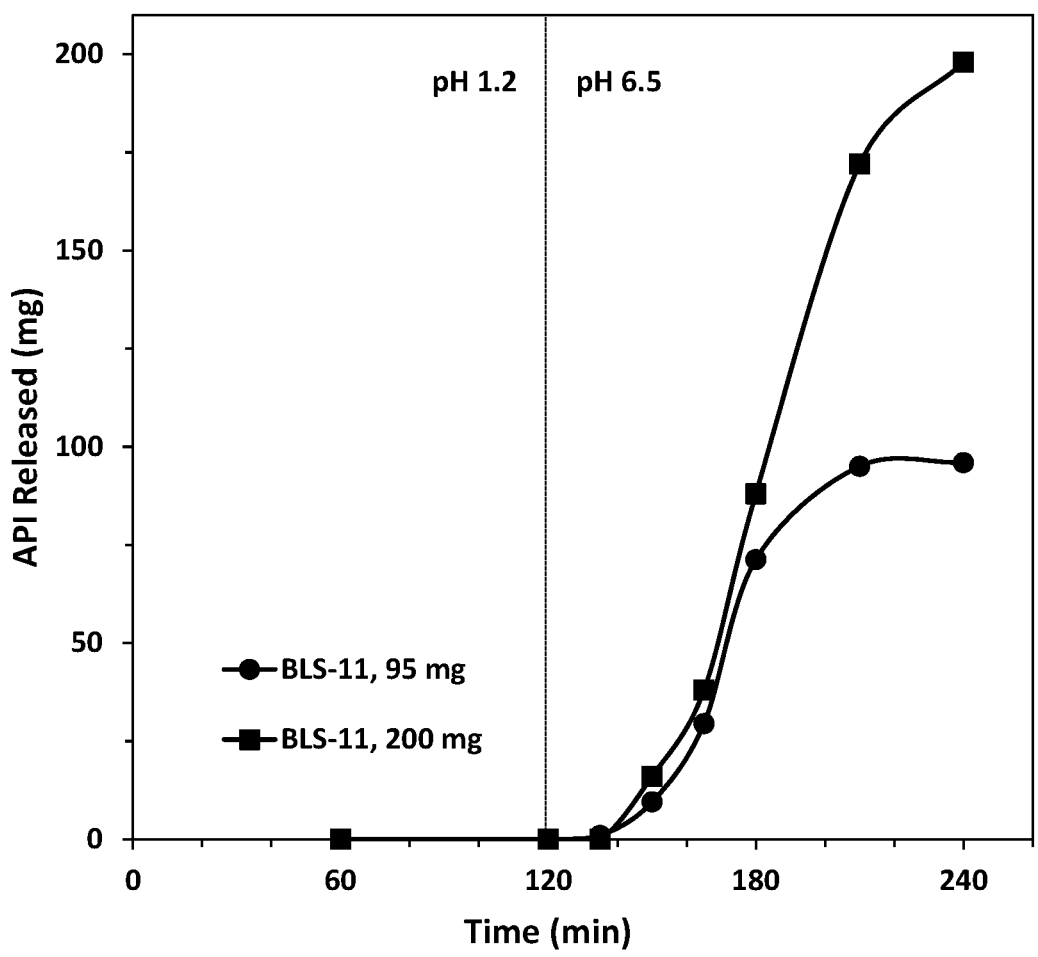
FIG. 2 shows BLS-11 release in two-stage dissolution experiments of dosage forms shown in Table 9.

The enterically coated soft capsules comprising the formulation shown in Table 9 were subject to two-stage dissolution experiments in a USP Apparatus 2 (e.g., stationary basket over paddle at 100 rpm in 900 mL of media, 37° C.) performed according to U.S. Pharmacopeial Convention Reference Standard Method ⟨711⟩ Dissolution. For these experiments, the capsules were introduced in to simulated gastric fluid, 0.1 N HCl, pH 1.2, for 2 hours. After 2 hours, the capsules were transferred to simulated intestinal fluid, phosphate buffer, pH 6.8. Aliquots of the media were removed at specific time points and analyzed by HPLC (Agilent Zorbax SB-Phenyl, 4.6×150 mm, 5 μm) with UV detection at 220 nm. Assays were performed in triplicate and the results averaged. The data is shown in Table 10 and the results are shown plotted in FIG. 1. The results show that the capsules retain their enteric properties for at least 2 hours in simulated gastric fluid at pH 1.2. The capsules began releasing the fumarate ester shortly (~15 minutes) after being transferred to simulated intestinal fluid, pH 6.8. About 50% of the capsule contents were released after about 52 min at pH 6.8 for the 95 mg dosage form. About 50% of the capsule contents were released after about 64 min at pH 6.8 for the 200 mg dosage form. The mass of fumarate ester (e.g., mg) released at each time point (shown in Table 10) is plotted in FIG. 2.

TABLE 10

Two-Stage Dissolution Experiment

| Time (min) | Cumulative Time | 95 mg API Dissolution (%) | 95 mg API Mass released (mg) | 200 mg API Dissolution (%) | 200 mg API Mass released (mg) |
|---|---|---|---|---|---|
| Time at pH 1.2 (SGF) (min) | | | | | |
| 60 | 60 | 0 | 0 | 0 | 0 |
| 120 | 120 | 0 | 0 | 0 | 0 |
| Time at pH 6.8 (SIF) (min) | | | | | |
| 15 | 135 | 1 | 0.95 | 0 | 0 |
| 30 | 150 | 10 | 9.5 | 8 | 16 |
| 45 | 165 | 31 | 29.45 | 19 | 38 |
| 60 | 180 | 75 | 71.25 | 44 | 88 |
| 90 | 210 | 100 | 95 | 86 | 172 |
| 120 | 240 | 101 | 95.95 | 99 | 198 |

The $T_{50}$ for the 95 mg dosage form is approximately 52 min at pH 6.8 (172 min cumulative)
The $T_{50}$ for the 200 mg dosage form is approximately 64 min at pH 6.8 (184 min cumulative)

Example 3

Two single-dose, randomized, open-label, two-way crossover, comparative bioavailability studies were conducted that compared two doses of BLS-11 (190 mg or 200 mg) to Tecfidera® 240 mg DMF delayed-release capsules. Fifty (50), healthy, adult male and non-pregnant female subjects were enrolled for each study. Subjects were randomized to one of two treatment sequences prior to the first dose.

In each period, subjects received a single oral dose of BLS-11 190 mg administered as two 95 mg delayed-release capsules (Test product A1), a single oral dose of BLS-11 200 mg delayed-release capsule (Test product A2), or a single dose of Tecfidera® 240 mg DMF delayed-release capsule (Reference product, B1 and B2), followed by blood sampling (including predose sample) up to 24 hours postdose for the determination of plasma concentrations of MMF. There was a washout period of at least 2 days between the two (Test or Reference) doses.

The Test product (for Treatment A1) was supplied as 95 mg delayed-release capsules (Banner Life Sciences) at Hour 0 on Day 1.

The Test product (for Treatment A2) was supplied as 200 mg delayed-release capsules (Banner Life Sciences) at Hour 0 on Day 1.

The Reference product (for Treatment B1 or B2) was supplied as Tecfidera® 240 mg DMF delayed-release capsules (Biogen, Inc.) at Hour 0 on Day 1.

All study drugs were administered with approximately 240 mL of water following an overnight (at least 10 hours) fast.

Blood samples for all subjects were collected in pre-chilled blood collection tubes containing sodium fluoride/potassium oxalate as the stabilizer and anticoagulant, respectively at scheduled time points direct venipuncture using a disposable sterile needle at each time of collection. Blood samples were collected at collected at pre-dose (0 hour), and at 0.5, 1, 1.5, 2, 2.5, 3, 3.5, 4, 4.5, 5, 5.5, 6, 8, 12 and 24-hours post-dose in each study period.

Samples were analyzed for plasma MMF concentrations using validated bioanalytical methods.

Example 4

Pharmacokinetic (PK) analyses of plasma concentration vs. time data of MMF were performed using noncompartmental methods with the following parameters calculated as appropriate or data permitting:

$AUC_{0 \to \tau}$: The area under the concentration-time curve, from time 0 (dosing time) to the last time point ($\tau_{last}$) with measurable drug concentration, as calculated by the linear trapezoidal method.

$AUC_{0 \to \infty}$: The area under the concentration-time curve from time 0 (dosing time) extrapolated to infinity. $AUC_{0 \to \infty}$ was calculated as the sum of $AUC_{0 \to \tau}$ plus the ratio of the last measurable drug concentration to the apparent terminal first-order decay rate constant.

$AUC_{\%\ extrap}$: Percent of $AUC_{0 \to \infty}$ extrapolated from the last time point with measurable drug concentration to infinity calculated as $(1 - AUC_{0 \to \tau}/AUC_{0 \to \infty}) \times 100$.

$C_{max}$: Maximum observed drug concentration.

$T_{max}$: Time to reach $C_{max}$. If the maximum value occurred at more than one time point, tmax was defined as the first time point with this value.

$k_{el}$: Apparent terminal first-order decay rate constant calculated from a semi-log plot of the plasma concentration-time curve. The parameter was calculated by linear least-squares regression analysis using at least three appropriate time points in the terminal log-linear phase.

$t_{1/2}$: Apparent plasma half-life calculated as $0.693/k_{el}$.

No values for $k_{el}$, $AUC_{0 \to \infty}$, $AUC_{\%\ extrap}$, or $t_{1/2}$ were reported for cases that did not exhibit an apparent terminal log-linear phase in the concentration-time profile. No parameters were calculated for subjects with three or fewer consecutive time points with detectable concentrations throughout the collection period.

The sample size was calculated using a power of at least 95% and an alpha error of 5%. The power was defined as the probability of having a 90% CI to a Test/Reference ratio within the acceptance criteria of 80.0-125.0%. A true ratio between 95-105% was assumed and an intra-subject CV of 24% was used. Fifty subjects were dosed in each study. This included six additional subjects to account for possible dropouts or non-evaluable data.

An ANOVA was performed on the ln-transformed $AUC_{0 \to \tau}$, $AUC_{0 \to \infty}$, and $C_{max}$ using SAS® Proc Mixed. The ANOVA model included sequence, treatment, and period as fixed effects, and subject nested within sequence as a random effect. Each ANOVA included calculation of least-squares means (LSM) of the ln-transformed parameter as well as the LSM difference between treatments.

Ratios of geometric LSM (GLSM) were calculated using the exponentiation of the difference between treatment LSM from the analyses on the ln-transformed $AUC_{0 \to \tau}$, $AUC_{0 \to \infty}$, and $C_{max}$. These ratios were expressed as a percentage, test relative to the reference (Treatment A vs. Treatment B).

Consistent with the two one-sided test, six 90% CIs for the GLSM ratios were derived by exponentiation of the CIs obtained for the LSM difference between treatments resulting from the analyses on the ln-transformed $AUC_{0 \to \tau}$, $AUC_{0 \to \infty}$, and $C_{max}$. The CIs were expressed as a percentage, test relative to the reference (Treatment A vs. Treatment B).

Bioequivalence criteria were met if the 90% CIs for the ratios of GLSMs of $C_{max}$ and $AUC_{0 \to \infty}$ of MMF of the Test (Treatment A1 or A2) to the Reference (Treatment B1 or B2) fall within the limit of 80.0 and 125.0%.

Time to maximal drug concentration, tmax, will also be analyzed without transformation using a non-parametric method (Wilcoxon test). This analysis was performed for information purpose, not for biequvalence assessment.

Figure 3:
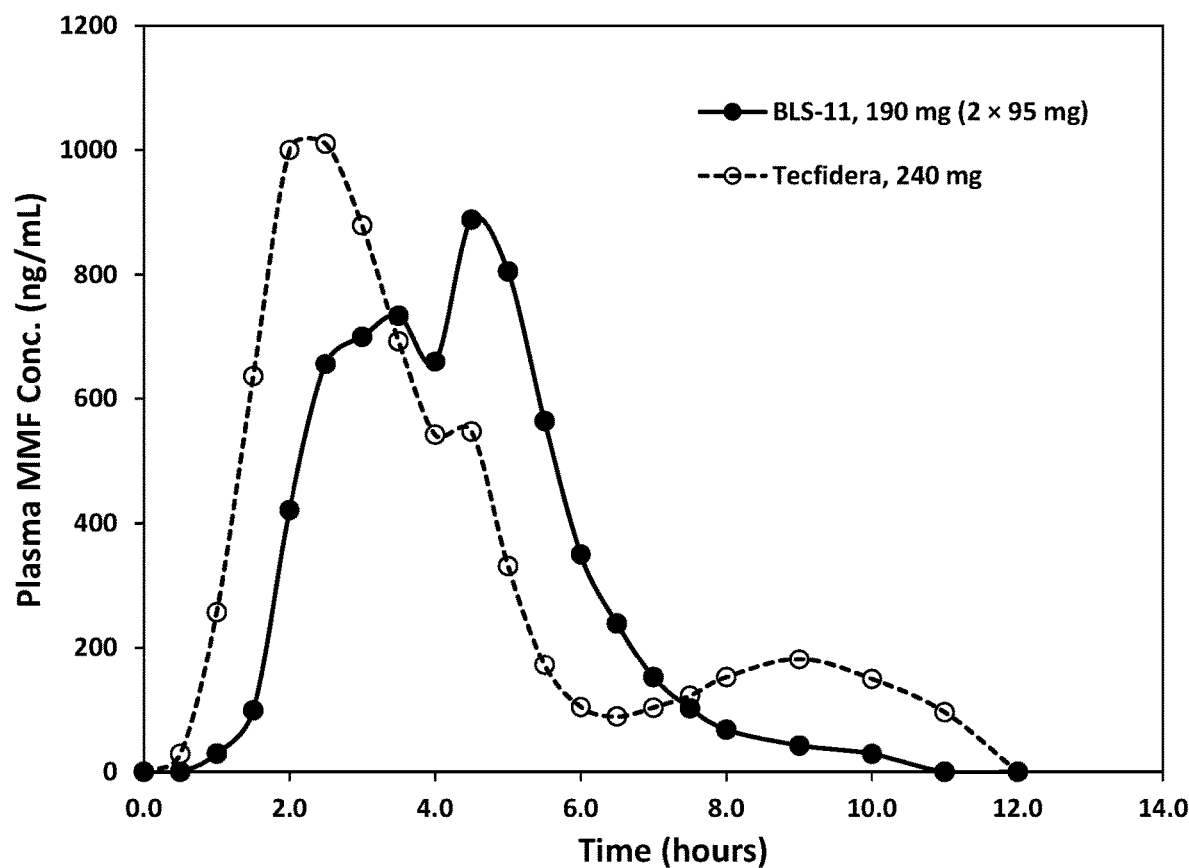
FIG. 3 shows plasma monomethyl fumarate concentrations as a function of time after administration of 190 mg of BLS-11.
Figure 4:
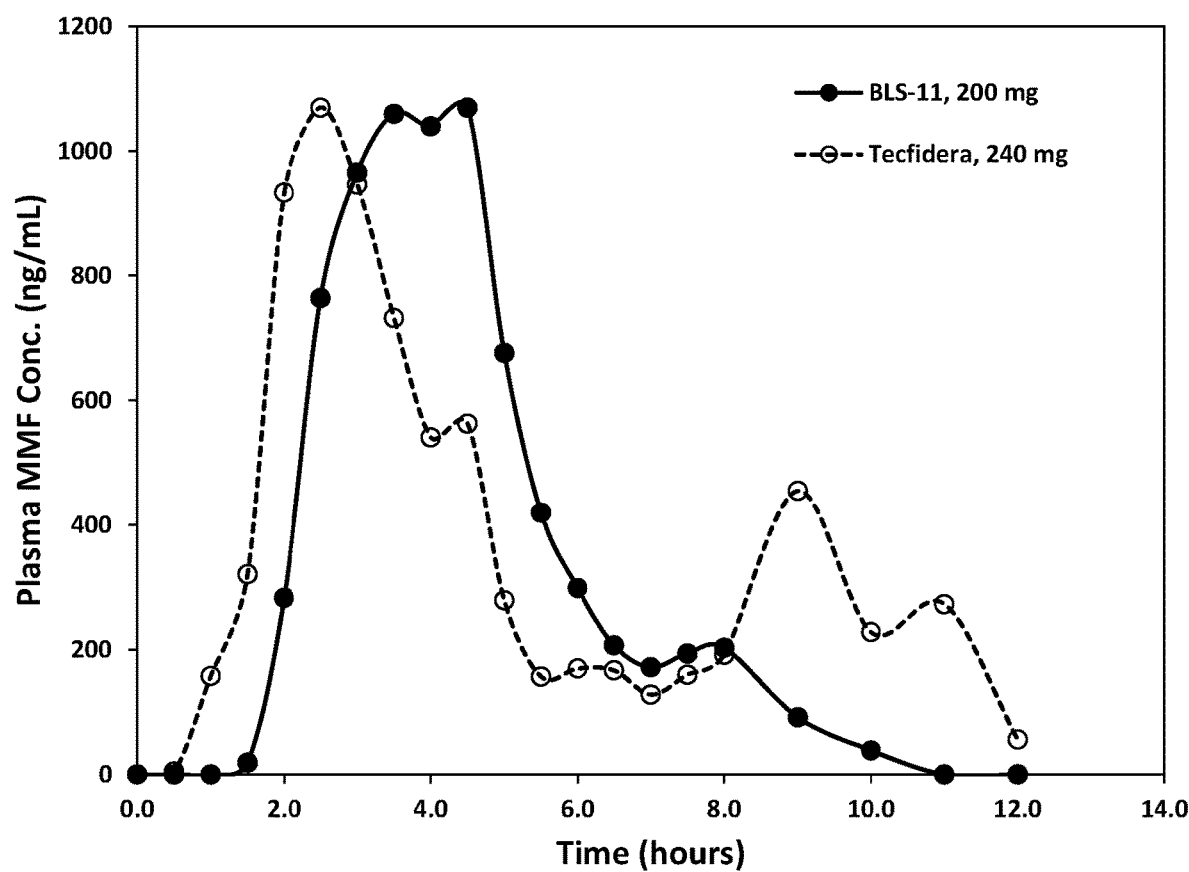
FIG. 4 shows plasma monomethyl fumarate concentrations as a function of time after administration of 200 mg of BLS-11.

The results of Test A1 and Reference B1 are shown in Tables 11-14 and FIG. 3. The results of Study A2 vs. Reference B2 are shown in Tables 15-18 and FIG. 4. A summary of the pharmacokinetic parameters for Test A1, Reference B1, Test A2, and Reference B2 is shown in Table 19.

TABLE 11

Plasma MMF Concentrations (ng/mL) BLS-11, 190 mg (2 × 95 mg) (Test A1)

| Time (h) | 0 | 0.5 | 1 | 1.5 | 2 | 2.5 | 3 | 3.5 | 4 | 4.5 | 5 |
|---|---|---|---|---|---|---|---|---|---|---|---|
| n | 50 | 50 | 50 | 50 | 50 | 50 | 50 | 50 | 50 | 50 | 49 |
| Mean | 0 | 0 | 29 | 98.4 | 421 | 656 | 700 | 734 | 660 | 888 | 805 |
| Std. Dev | 0 | 0 | 175 | 287 | 673 | 757 | 777 | 692 | 672 | 855 | 779 |
| SEM | 0 | 0 | 24.8 | 40.6 | 95.1 | 107 | 110 | 97.9 | 95 | 121 | 111 |
| Minimum | 0 | 0 | 0 | 0 | 0 | 0 | 0 | 0 | 0 | 0 | 25.6 |
| Median | 0 | 0 | 0 | 0 | 0 | 214 | 583 | 592 | 507 | 667 | 518 |
| Maximum | 0 | 0 | 1230 | 1400 | 2320 | 2310 | 3070 | 2380 | 3470 | 4060 | 2700 |
| CV % | . | . | 603.4 | 291.5 | 159.7 | 115.4 | 110.9 | 94.3 | 101.8 | 96.3 | 96.7 |

| Time: | 5.5 | 6 | 6.5 | 7 | 7.5 | 8 | 9 | 10 | 11 | 12 | 24 |
|---|---|---|---|---|---|---|---|---|---|---|---|
| n | 48 | 43 | 36 | 28 | 21 | 15 | 5 | 1 | 0 | 0 | 0 |
| Mean | 564 | 350 | 239 | 152 | 102 | 67.6 | 42.1 | 28.7 | . | . | . |
| Std. Dev | 602 | 366 | 262 | 156 | 89.8 | 49.2 | 20.5 | . | . | . | . |
| SEM | 86.9 | 55.8 | 43.7 | 29.6 | 19.6 | 12.7 | 9.15 | . | . | . | . |
| Minimum | 26.7 | 26.3 | 26.2 | 25.5 | 25.5 | 25.5 | 25.8 | 28.7 | . | . | . |
| Median | 224 | 199 | 142 | 109 | 69.2 | 50.5 | 28.8 | 28.7 | . | . | . |
| Maximum | 2120 | 1390 | 1080 | 702 | 405 | 204 | 66.7 | 28.7 | . | . | . |
| CV % | 106.6 | 104.6 | 110 | 103.1 | 88 | 72.8 | 48.6 | . | . | . | . |

For the calculation of summary statistics, values that are below the limit of quantitation (BLQ) of 25 ng/mL are treated as 0 prior to $T_{max}$ and as missing thereafter "." Indicates value missing or not reportable.

TABLE 12

BLS-11, 190 mg (2 × 95 mg) (Test A1)

|  | $AUC_{0 \to \tau}$ (hr·ng/mL) | $AUC_{0 \to \infty}$ (hr·ng/mL) | $AUC_{\% \, extrap}$ (%) | $C_{max}$ (ng/mL) | $T_{max}$ (hr) | $K_{el}$ (hr$^{-1}$) | $t_{1/2}$ (hr) |
|---|---|---|---|---|---|---|---|
| n | 50 | 48 | 48 | 50 | 50 | 48 | 48 |
| Mean | 3060 | 3080 | 1.04 | 1860 | 3.82 | 1.35 | 0.533 |
| Std. Dev | 814 | 825 | 0.781 | 600 | 1.21 | 0.243 | 0.12 |
| CV % | 26.6 | 26.8 | 75 | 32.2 | 31.7 | 18 | 22.6 |
| SEM | 115 | 119 | 0.113 | 84.8 | 0.171 | 0.0351 | 0.0174 |
| Minimum | 1560 | 1590 | 0.358 | 524 | 1 | 0.608 | 0.355 |
| Median | 3040 | 3030 | 0.845 | 1860 | 4.25 | 1.33 | 0.52 |
| Maximum | 6020 | 6040 | 5.48 | 4060 | 6 | 1.95 | 1.14 |
| Geom. Mean | 2960 | 2980 | 0.907 | 1770 | 3.59 | 1.33 | 0.522 |
| Geom. CV % | 26.7 | 26.6 | 50 | 34.5 | 39.3 | 19.6 | 19.6 |

TABLE 13

Tecfidera ® 240 mg (1 × 240 mg) DMF (Reference B1)

|  | $AUC_{0 \to \tau}$ (hr·ng/mL) | $AUC_{0 \to \infty}$ (hr·ng/mL) | $AUC_{\% \, extrap}$ (%) | $C_{max}$ (ng/mL) | $T_{max}$ (hr) | $K_{el}$ (hr$^{-1}$) | $t_{1/2}$ (hr) |
|---|---|---|---|---|---|---|---|
| n | 49 | 46 | 46 | 49 | 49 | 46 | 46 |
| Mean | 3130 | 3210 | 0.964 | 1770 | 2.72 | 1.31 | 0.558 |
| Std. Dev | 789 | 782 | 0.569 | 580 | 1.04 | 0.291 | 0.15 |
| CV % | 25.2 | 24.4 | 59 | 32.7 | 38 | 22.1 | 26.9 |
| SEM | 113 | 115 | 0.0839 | 82.8 | 0.148 | 0.0429 | 0.0221 |
| Minimum | 1940 | 1970 | 0.4 | 763 | 1 | 0.658 | 0.355 |
| Median | 3050 | 3120 | 0.817 | 1650 | 2.5 | 1.34 | 0.517 |
| Maximum | 5790 | 5820 | 3.7 | 3500 | 5 | 1.95 | 1.05 |
| Geom. Mean | 3040 | 3120 | 0.857 | 1680 | 2.54 | 1.28 | 0.542 |
| Geom. CV % | 49 | 46 | 46 | 49 | 49 | 46 | 46 |

TABLE 14

Test A1 vs. Reference B1
BLS-11, 190 mg (2 × 95 mg) (Test A1) vs. Tecfidera ®
240 mg (1 × 240 mg) DMF (Reference B1)

| Parameters | Test Geometric LSM | Reference Geometric LSM | Geometric Mean Ratio | Lower 90% CI | Upper 90% CI | Intra-Subject CV % |
|---|---|---|---|---|---|---|
| $AUC_{0 \to \tau}$ (hr·ng/mL) | 2950 | 3040 | 97.09 | 92.32 | 102.12 | 14.96 |
| $AUC_{0 \to \infty}$ (hr·ng/mL) | 3040 | 3120 | 97.34 | 92.48 | 102.44 | 14.67 |
| $C_{max}$ (ng/mL) | 1760 | 1680 | 104.84 | 95.54 | 115.05 | 27.93 |

Test A1: An oral dose of BLS-11 190 mg (2 × 95 mg)
Reference B1: A single oral dose of Tecfidera ® 240 mg (1 × 240 mg) DMF
Geometric least-squares means (LSMs) are calculated by exponentiating the LSMs derived from the ANOVA
Geometric Mean Ratio (GMR) = 100 × (Test/Reference)
Intra-subject CV % = 100 × square root(exp[MSE]$^{-1}$), where MSE is the Residual Variance from ANOVA

TABLE 15

Plasma MMF Concentrations (ng/mL) BLS-11, 200 mg (1 × 20 mg) (Test A2)

| Time (h) | 0 | 0.5 | 1 | 1.5 | 2 | 2.5 | 3 | 3.5 | 4 | 4.5 | 5 |
|---|---|---|---|---|---|---|---|---|---|---|---|
| n | 49 | 49 | 49 | 49 | 48 | 49 | 49 | 49 | 47 | 49 | 49 |
| Mean | 0 | 0 | 0 | 19 | 283 | 764 | 966 | 1060 | 1040 | 1070 | 676 |
| Std. Dev | 0 | 0 | 0 | 133 | 1010 | 1180 | 1080 | 866 | 834 | 969 | 807 |
| SEM | 0 | 0 | 0 | 19 | 146 | 168 | 154 | 124 | 122 | 138 | 115 |
| Minimum | 0 | 0 | 0 | 0 | 0 | 0 | 0 | 0 | 0 | 0 | 29 |

TABLE 15-continued

| Plasma MMF Concentrations (ng/mL) BLS-11, 200 mg (1 × 20 mg) (Test A2) | | | | | | | | | | |
|---|---|---|---|---|---|---|---|---|---|---|
| Median | 0 | 0 | 0 | 0 | 0 | 120 | 691 | 1020 | 861 | 725 | 397 |
| Maximum | 0 | 0 | 0 | 930 | 6380 | 5270 | 3660 | 3560 | 3530 | 3420 | 3500 |
| CV % | . | . | . | 700 | 356.9 | 154.3 | 111.5 | 81.9 | 80 | 90.7 | 119.4 |

| Time: | 5.5 | 6 | 6.5 | 7 | 7.5 | 8 | 9 | 10 | 11 | 12 | 24 |
|---|---|---|---|---|---|---|---|---|---|---|---|
| n | 47 | 40 | 32 | 24 | 13 | 7 | 4 | 2 | 0 | 0 | 0 |
| Mean | 420 | 299 | 207 | 172 | 194 | 203 | 91.7 | 38.7 | . | . | . |
| Std. Dev | 543 | 419 | 320 | 302 | 303 | 259 | 60.7 | 5.52 | . | . | . |
| SEM | 79.2 | 66.3 | 56.6 | 61.7 | 83.9 | 97.8 | 30.4 | 3.9 | . | . | . |
| Minimum | 29.4 | 29.4 | 25.5 | 26.8 | 28.2 | 26.9 | 35.6 | 34.8 | . | . | . |
| Median | 197 | 105 | 77.5 | 52.8 | 59.8 | 134 | 82.6 | 38.7 | . | . | . |
| Maximum | 2410 | 1860 | 1410 | 1380 | 1110 | 758 | 166 | 42.6 | . | . | . |
| CV % | 129.1 | 140.2 | 154.3 | 175.7 | 156.1 | 127.4 | 66.2 | 14.3 | . | . | . |

For the calculation of summary statistics, values that are below the limit of quantitation (BLQ) of 25 ng/mL are treated as 0 prior to $T_{max}$ and as missing thereafter
"." Indicates value missing or not reportable

TABLE 16

| BLS-11 200 mg (1 × 200 mg) (Test A2) | | | | | | | |
|---|---|---|---|---|---|---|---|
| | $AUC_{0\to\tau}$ (hr · ng/mL) | $AUC_{0\to\infty}$ (hr · ng/mL) | $AUC_{\% extrap}$ (%) | $C_{max}$ (ng/mL) | $T_{max}$ (hr) | $K_{el}$ (hr$^{-1}$) | $t_{1/2}$ (hr) |
| n | 49 | 49 | 49 | 49 | 49 | 49 | 49 |
| Mean | 3440 | 3470 | 0.855 | 2370 | 3.84 | 1.43 | 0.497 |
| Std. Dev | 1150 | 1150 | 0.329 | 1090 | 0.965 | 0.232 | 0.0889 |
| CV % | 33.5 | 33.2 | 38.4 | 45.8 | 25.2 | 16.2 | 17.9 |
| SEM | 164 | 164 | 0.047 | 155 | 0.138 | 0.0331 | 0.0127 |
| Minimum | 1580 | 1610 | 0.346 | 883 | 2 | 0.916 | 0.354 |
| Median | 3360 | 3380 | 0.785 | 2260 | 4 | 1.48 | 0.467 |
| Maximum | 7360 | 7390 | 1.65 | 6380 | 6.5 | 1.96 | 0.757 |
| Geom. Mean | 3260 | 3290 | 0.794 | 2160 | 3.72 | 1.41 | 0.49 |
| Geom. CV % | 33.7 | 33.4 | 40.9 | 46.5 | 26 | 17.1 | 17.1 |

TABLE 17

| Tecfidera ® 240 mg (1 × 240 mg) DMF (Reference B2) | | | | | | | |
|---|---|---|---|---|---|---|---|
| | $AUC_{0\to\tau}$ (hr · ng/mL) | $AUC_{0\to\infty}$ (hr · ng/mL) | $AUC_{\% extrap}$ (%) | $C_{max}$ (ng/mL) | $T_{max}$ (hr) | $K_{el}$ (hr$^{-1}$) | $t_{1/2}$ (hr) |
| n | 50 | 44 | 44 | 50 | 50 | 44 | 44 |
| Mean | 3120 | 3170 | 0.924 | 1870 | 3.06 | 1.37 | 0.523 |
| Std. Dev | 774 | 776 | 0.455 | 692 | 1.45 | 0.234 | 0.106 |
| CV % | 24.8 | 24.5 | 49.2 | 36.9 | 47.2 | 17.1 | 20.3 |
| SEM | 109 | 117 | 0.0686 | 97.8 | 0.204 | 0.0353 | 0.016 |
| Minimum | 1700 | 1720 | 0.347 | 613 | 1 | 0.73 | 0.383 |
| Median | 3240 | 3310 | 0.772 | 1800 | 2.5 | 1.37 | 0.506 |
| Maximum | 5180 | 5200 | 2.2 | 3650 | 9 | 1.81 | 0.95 |
| Geom. Mean | 3030 | 3070 | 0.834 | 1750 | 2.81 | 1.35 | 0.514 |
| Geom. CV % | 26.1 | 25.7 | 46.5 | 40.4 | 42.5 | 18.5197 | 18.5 |

TABLE 18

| Test A2 vs. Reference B2 | | | | | | |
|---|---|---|---|---|---|---|
| Parameters | Test Geometric LSM | Reference Geometric LSM | Geometric Mean Ratio | Lower 90% CI | Upper 90% CI | Intra-Subject CV % |
| $AUC_{0\to\tau}$ (hr · ng/mL) | 3270 | 3020 | 108.07 | 101.74 | 114.79 | 17.94 |
| $AUC_{0\to\infty}$ (hr · ng/mL) | 3390 | 3070 | 110.63 | 104 | 117.69 | 17.16 |

TABLE 18-continued

Test A2 vs. Reference B2

| Parameters | Test Geometric LSM | Reference Geometric LSM | Geometric Mean Ratio | Lower 90% CI | Upper 90% CI | Intra-Subject CV % |
|---|---|---|---|---|---|---|
| $C_{max}$ (ng/mL) | 2150 | 1740 | 124.14 | 110.47 | 139.5 | 35.44 |

Test A2: A single oral dose of BLS-11 200 mg (1 × 200 mg)
Reference B2: A single oral dose of Tecfidera ® 240 mg (1 × 240 mg) DMF
Geometric least-squares means (LSMs) are calculated by exponentiating the LSMs derived from the ANOVA
Geometric Mean Ratio (GMR) = 100 × (Test/Reference)
Intra-subject CV % = 100 × square root(exp[MSE]$^{-1}$), where MSE is the Residual Variance from ANOVA

TABLE 19

Summary of Pharmacokinetic Parameters

| | $AUC_{0 \to \tau}$ (hr · ng/mL) | $AUC_{0 \to \infty}$ (hr · ng/mL) | $AUC_{\% \, extrap}$ (%) | $C_{max}$ (ng/mL) | $T_{max}$ (hr) | $K_{el}$ (hr$^{-1}$) | $t_{1/2}$ (hr) |
|---|---|---|---|---|---|---|---|
| BLS-11, 190 mg | 3060 | 3080 | 1.04 | 1860 | 3.82 | 1.35 | 0.533 |
| Std Dev. | 814 | 825 | 0.781 | 600 | 1.21 | 0.243 | 0.12 |
| Tecfidera, 240 mg DMF | 3130 | 3210 | 0.964 | 1770 | 2.72 | 1.31 | 0.558 |
| Std Dev. | 789 | 782 | 0.569 | 580 | 1.04 | 0.291 | 0.15 |
| BLS-11, 200 mg | 3440 | 3470 | 0.855 | 2370 | 3.84 | 1.43 | 0.497 |
| Std Dev. | 1150 | 1150 | 0.329 | 1090 | 0.965 | 0.232 | 0.0889 |
| Tecfidera, 240 mg DMF | 3120 | 3170 | 0.924 | 1870 | 3.06 | 1.37 | 0.523 |
| Std Dev. | 774 | 776 | 0.455 | 692 | 1.45 | 0.234 | 0.106 |

The invention claimed is:

1. A pharmaceutical dosage form comprising a soft capsule and matrix fill comprising about 85 mg to about 100 mg of monomethyl fumarate suspended in an immediate releasing single-phase non-aqueous liquid vehicle, wherein contemporaneous administration to a subject of two dosage forms provides one or more of pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\% \, ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

2. The dosage form of claim 1, wherein the immediate releasing single-phase non-aqueous liquid vehicle comprises a mixture of mono- and di-glycerides, polyvinylpyrrolidone, polyoxyl 40 hydrogenated castor oil, and lactic acid.

3. The dosage form of claim 1, wherein the soft capsule is enterically coated.

4. The dosage form of claim 1, wherein contemporaneous administration of two dosage forms to a subject provides pharmacokinetic parameters that are bioequivalent to a single 240 mg dose of dimethyl fumarate.

5. The dosage form of claim 1, wherein the dosage form releases about 50% of the monomethyl fumarate after about 50 min to about 65 min in sodium phosphate, pH 6.8, in a USP Apparatus 2 at 37° C.

6. The dosage form of claim 1, wherein the matrix fill comprises:
(a) about 30% to about 35% by mass monomethyl fumarate;
(b) about 20% to about 50% by mass mono- and di-glycerides;
(c) about 0.75% to about 5% by mass polyvinyl pyrrolidone;
(e) about 2% to about 12% by mass polyoxyl 40 hydrogenated castor oil; and
(e) about 1% to about 5% by mass lactic acid.

7. A pharmaceutical dosage form comprising a soft capsule and matrix fill comprising about 160 mg to about 200 mg of monomethyl fumarate suspended in an immediate releasing single-phase non-aqueous liquid vehicle, wherein administration of one dosage form to a subject provides one or more pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr·ng/mL; (e) a mean plasma monomethyl fumarate $AUC_{\% \, ex}$ of about 0.86%; (f) a mean plasma monomethyl fumarate $K_{el}$ of about 1.4 hr$^{-1}$; or (g) a mean plasma monomethyl fumarate $t_{1/2}$ of about 0.5 hr.

8. The dosage form of claim 7, wherein the immediate releasing single-phase non-aqueous liquid vehicle comprises a mixture of mono- and di-glycerides, polyvinylpyrrolidone, polyoxyl 40 hydrogenated castor oil, and lactic acid.

9. The dosage form of claim 7, wherein the soft capsule is enterically coated.

10. A method for treating or reducing symptoms of multiple sclerosis in a subject comprising contemporaneously administering to a subject in need thereof two pharmaceutical dosage forms comprising an enterically coated soft capsule comprising a matrix fill comprising about 80 mg to about 100 mg of monomethyl fumarate suspended in an immediate releasing single-phase non-aqueous liquid vehicle that provides one or more pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\% \, ex}$ of about 1.0%; (f) a mean plasma monomethyl fumarate $K_{el}$ of about 1.4 hr$^{-1}$; or (g) a mean plasma monomethyl fumarate $t_{1/2}$ of about 0.5 hr.

11. The method of claim 10, wherein contemporaneous administration of two dosage forms to a subject provides pharmacokinetic parameters that are bioequivalent to a single 240 mg dose of dimethyl fumarate.

12. The method of claim 10, wherein 170 mg to about 200 mg of monomethyl fumarate is administered at each dosage.

\* \* \* \* \*